United States Patent
Schuster

(10) Patent No.: US 9,839,433 B2
(45) Date of Patent: Dec. 12, 2017

(54) DEVICE FOR THE RESECTION OF BONES, METHOD FOR PRODUCING SUCH A DEVICE, ENDOPROSTHESIS SUITED FOR THIS PURPOSE AND METHOD FOR PRODUCING SUCH AN ENDOPROSTHESIS

(71) Applicant: Biomet Manufacturing, LLC, Warsaw, IN (US)

(72) Inventor: Luis Schuster, Stamberg (DE)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/183,349

(22) Filed: Jun. 15, 2016

(65) Prior Publication Data
US 2016/0296240 A1 Oct. 13, 2016

Related U.S. Application Data

(63) Continuation of application No. 13/389,700, filed as application No. PCT/EP2010/061630 on Aug. 10, 2010, now Pat. No. 9,393,028.

(30) Foreign Application Priority Data

Aug. 13, 2009 (DE) ........................ 10 2009 028 503

(51) Int. Cl.
*A61B 17/15* (2006.01)
*A61F 2/38* (2006.01)
*A61F 2/30* (2006.01)

(52) U.S. Cl.
CPC .......... *A61B 17/154* (2013.01); *A61B 17/155* (2013.01); *A61B 17/157* (2013.01);
(Continued)

(58) Field of Classification Search
CPC .... A61B 17/154; A61B 17/155; A61B 17/157
See application file for complete search history.

(56) References Cited

U.S. PATENT DOCUMENTS

| 1,480,285 A | 1/1924 | Moore |
|---|---|---|
| 2,181,746 A | 11/1939 | Siebrandt |

(Continued)

FOREIGN PATENT DOCUMENTS

| CA | 2447694 A1 | 12/2002 |
|---|---|---|
| CA | 2501041 A1 | 4/2004 |

(Continued)

OTHER PUBLICATIONS

"Amazing Precision. Beautiful Results. The next evolution of MAKOplasty® is here", MAKO Surgical Corp., (Feb. 2009), 6 pgs.
(Continued)

*Primary Examiner* — Christian Sevilla
(74) *Attorney, Agent, or Firm* — Schwegman Lundberg & Woessner, P.A.

(57) ABSTRACT

The present invention refers to a device for the resection of bones (1) for preparing the attachment of an endoprosthesis to the joints which consists of at least two joint elements cooperating with each other, comprising at least one tool guide (3, 4, 5, 7, 14) and at least one support (6, 9, 10, 15, 21) suitable for orienting the at least one tool guide (3, 4, 5, 7, 14), wherein, either in the immediate vicinity of the joint and/or across joints, the at least one support (15, 21) enables the at least one tool guide (3, 4, 5, 7, 14) to be oriented and positioned on a further joint element, or enables the at least one tool guide (3, 4, 5, 7, 14) to be oriented and positioned at the same joint element distally to the area to be treated and/or outside the surgical area. The at least one tool guide (3, 4, 5, 7, 14) and the at least one support are preferably immovably connected to each other so as to manufacture an individual single-use template. The invention also relates to
(Continued)

Figure 1:
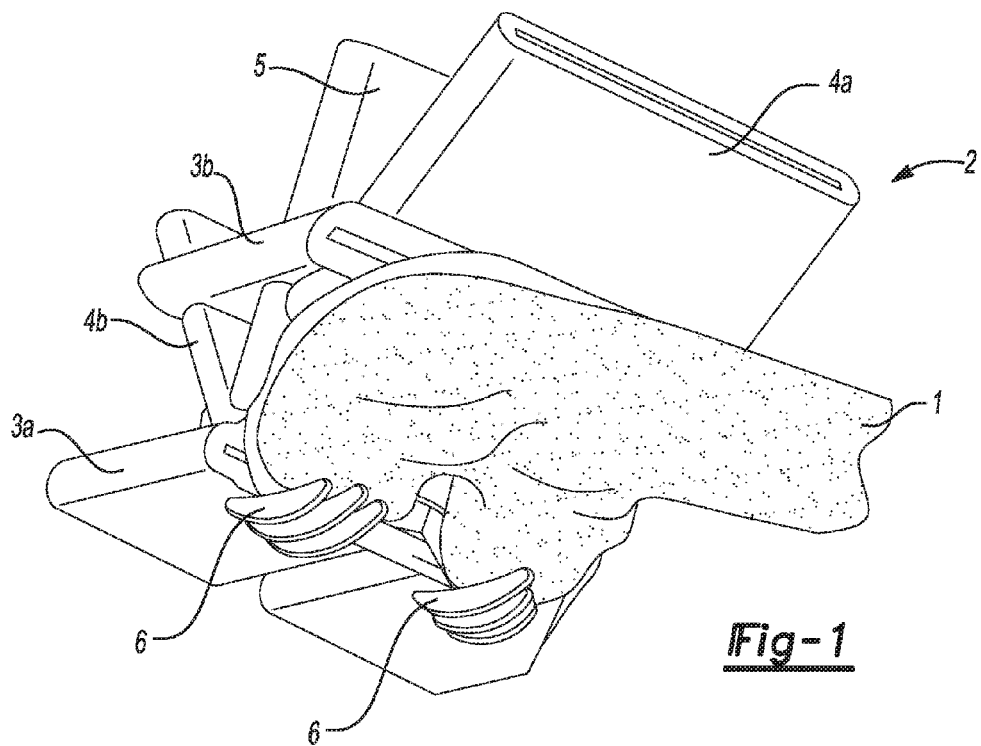

a method for manufacturing such a device or template, an endoprosthesis suited for this purpose, a method for manufacturing such an endoprosthesis, and a surgical set consisting of said parts.

25 Claims, 11 Drawing Sheets

(52) U.S. Cl.
CPC ............ *A61F 2/389* (2013.01); *A61F 2/3859* (2013.01); *A61F 2002/30948* (2013.01); *A61F 2002/30962* (2013.01); *Y10T 29/49* (2015.01)

(56) References Cited

U.S. PATENT DOCUMENTS

| | | |
|---|---|---|
| 2,407,845 A | 9/1946 | Orisan |
| 2,416,228 A | 2/1947 | Sheppard |
| 2,618,913 A | 11/1952 | Plancon et al. |
| 2,910,978 A | 11/1959 | Urist |
| 3,330,611 A | 7/1967 | Heifetz |
| 3,840,904 A | 10/1974 | Tronzo |
| 3,975,858 A | 8/1976 | Much |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,528,980 A | 7/1985 | Kenna |
| 4,565,191 A | 1/1986 | Slocum |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,006,121 A | 4/1991 | Hafeli |
| 5,007,936 A | 4/1991 | Woolson |
| 5,030,219 A | 7/1991 | Matsen et al. |
| 5,030,221 A | 7/1991 | Buechel et al. |
| 5,041,117 A | 8/1991 | Engelhardt |
| 5,053,037 A | 10/1991 | Lackey |
| 5,053,039 A | 10/1991 | Hofmann et al. |
| 5,056,351 A | 10/1991 | Stiver et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,194,066 A | 3/1993 | Van Zile |
| 5,234,433 A | 8/1993 | Bert et al. |
| 5,246,444 A | 9/1993 | Schreiber |
| 5,253,506 A | 10/1993 | Davis et al. |
| 5,258,032 A | 11/1993 | Bertin |
| 5,261,915 A | 11/1993 | Durlacher et al. |
| 5,274,565 A | 12/1993 | Reuben |
| 5,282,802 A | 2/1994 | Mahony, III |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,593,411 A | 1/1997 | Stalcup et al. |
| 5,595,703 A | 1/1997 | Swaelens et al. |
| 5,601,563 A | 2/1997 | Burke et al. |
| 5,601,565 A | 2/1997 | Huebner |
| 5,607,431 A | 3/1997 | Dudasik et al. |
| 5,611,802 A | 3/1997 | Samuelson et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,653,714 A | 8/1997 | Dietz et al. |
| 5,658,294 A | 8/1997 | Sederholm |
| 5,662,656 A | 9/1997 | White |
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |

(56) References Cited

U.S. PATENT DOCUMENTS

| | | |
|---|---|---|
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,697,933 A | 12/1997 | Gundlapalli et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliot et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,766,251 A | 6/1998 | Koshino |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,835,619 A | 11/1998 | Morimoto et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,008,433 A | 12/1999 | Stone |
| 6,019,767 A | 2/2000 | Howell |
| 6,033,415 A | 3/2000 | Mittelstadt et al. |
| 6,042,612 A | 3/2000 | Voydeville |
| 6,056,754 A | 5/2000 | Haines et al. |
| 6,059,789 A | 5/2000 | Dinger |
| 6,059,833 A | 5/2000 | Doets |
| 6,066,175 A | 5/2000 | Henderson et al. |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,187,010 B1 | 2/2001 | Masini |
| 6,195,615 B1 | 2/2001 | Lysen |
| 6,203,546 B1 | 3/2001 | Macmahon |
| 6,205,411 B1 | 3/2001 | Digioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,829 B1 | 12/2001 | Schmotzer |
| 6,327,491 B1 | 12/2001 | Franklin et al. |
| 6,338,738 B1 | 1/2002 | Bellotti et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,424,332 B1 | 7/2002 | Powell |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,610,067 B2 | 8/2003 | Tallarida et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,676,892 B2 | 1/2004 | Das et al. |
| 6,682,566 B2 | 1/2004 | Draenert et al. |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladiono |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford |
| 6,923,817 B2 | 8/2005 | Carson et al. |

(56) References Cited

U.S. PATENT DOCUMENTS

| | | |
|---|---|---|
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | Disilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | Mclean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma De La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-schäffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,690 B2 | 11/2010 | Metzger |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roβner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaβky et al. |
| 8,313,491 B2 | 11/2012 | Green, II et al. |
| D672,038 S | 12/2012 | Frey |
| 8,333,772 B2 | 12/2012 | Fox et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |

(56) References Cited

U.S. PATENT DOCUMENTS

| | | |
|---|---|---|
| 8,407,067 B2 | 3/2013 | Uthgenannt et al. |
| 8,414,594 B2 | 4/2013 | Berger et al. |
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite et al. |
| 8,979,936 B2 | 3/2015 | White et al. |
| 9,005,297 B2 | 4/2015 | Katrana et al. |
| 2001/0005797 A1 | 6/2001 | Barlow et al. |
| 2001/0011190 A1 | 8/2001 | Park |
| 2001/0021876 A1 | 9/2001 | Terril-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Denny, III |
| 2004/0220583 A1 | 11/2004 | Pieczynski, II et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | De La Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209605 A1 | 9/2005 | Grimm et al. |
| 2005/0216305 A1 | 9/2005 | Funderud |

(56) References Cited

U.S. PATENT DOCUMENTS

| | | |
|---|---|---|
| 2005/0222571 A1 | 10/2005 | Ryan |
| 2005/0222573 A1 | 10/2005 | Branch et al. |
| 2005/0234461 A1 | 10/2005 | Burdulis, Jr. et al. |
| 2005/0234465 A1 | 10/2005 | Mccombs et al. |
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady, Jr. et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233266 A1* | 10/2007 | Williams, III ............ A61F 2/36 623/20.14 |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |

(56) References Cited

U.S. PATENT DOCUMENTS

| | | |
|---|---|---|
| 2008/0195099 A1 | 8/2008 | Minas |
| 2008/0195107 A1 | 8/2008 | Cuckler et al. |
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Worner et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1* | 4/2009 | Aram ............... A61B 17/155 606/79 |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |

(56) References Cited

U.S. PATENT DOCUMENTS

| | | |
|---|---|---|
| 2010/0281678 A1 | 11/2010 | Burdulis, Jr. et al. |
| 2010/0286700 A1 | 11/2010 | Snider et al. |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0192401 A1 | 8/2012 | Pavlovskaia et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0259335 A1 | 10/2012 | Scifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0197528 A1 | 8/2013 | Zakaria et al. |
| 2013/0197529 A1 | 8/2013 | Metzger |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman |
| 2013/0264749 A1 | 10/2013 | Jones et al. |
| 2013/0268085 A1 | 10/2013 | Dong et al. |
| 2013/0289730 A1 | 10/2013 | Gabriel et al. |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |

(56) References Cited

U.S. PATENT DOCUMENTS

| | | |
|---|---|---|
| 2014/0066937 A1 | 3/2014 | Wiebe, III et al. |
| 2014/0081275 A1 | 3/2014 | Metzger et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0127211 A1 | 5/2014 | Geles et al. |
| 2014/0135775 A1 | 5/2014 | Maxson |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| DE | 3447365 A1 | 7/1986 |
| DE | 04219939 A1 | 12/1993 |
| DE | 4421153 A1 | 12/1995 |
| DE | 4434539 C2 | 6/1998 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1074229 A2 | 2/2001 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 1852072 A3 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A2 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A1 | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 6233790 A | 8/1994 |
| JP | 2000245758 A | 9/2000 |
| JP | 2005218861 A | 8/2005 |
| JP | 2009514612 A | 4/2009 |
| JP | 2011505080 A | 2/2011 |
| JP | 2011527885 A | 11/2011 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | 231755 A | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A2 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-20060149283 | 7/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |

(56) References Cited

FOREIGN PATENT DOCUMENTS

| WO | WO-2008101090 A2 | 8/2008 |
|---|---|---|
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011019797 A3 | 2/2011 |
| WO | WO-2011041398 A1 | 4/2011 |
| WO | WO-2011060536 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012158917 A1 | 11/2012 |
| WO | WO-2012173929 A1 | 12/2012 |
| WO | WO-2012174008 A1 | 12/2012 |
| WO | WO-2013170872 A1 | 11/2013 |
| WO | WO-2014019712 A1 | 2/2014 |

OTHER PUBLICATIONS

"U.S. Appl. No. 13/389,700, Non Final Office Action dated Oct. 8, 2015", 7 pgs.
"U.S. Appl. No. 13/389,700, Notice of Allowance dated Mar. 15, 2016", 6 pgs.
"U.S. Appl. No. 13/389,700, Preliminary Amendment filed Feb. 9, 2012", 11 pgs.
"U.S. Appl. No. 13/389,700, Response filed Jan. 4, 2016 to Non Final Office Action dated Oct. 8, 2015", 14 pgs.
"U.S. Appl. No. 13/389,700, Response filed Jul. 28, 2015 to Restriction Requirement dated Apr. 9, 2015", 8 pgs.
"U.S. Appl. No. 13/389,700, Restriction Requirement dated Apr. 9, 2015", 7 pgs.
"Ascent Total Knee System", Biomet, Inc., (Oct. 31, 1999), 16 pgs.
"Australian Application Serial No. 2013222609, First Examiner Report dated Feb. 16, 2015", 5 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.
"Customized Patient Instruments, Primary Cruciate Retaining Surgical Technique for use with the Sigma® Knee System Utilizing Specialist® 2 Instrumentation", DePuy Orthopaedics, Inc., (2008), 1-23.
"Discovery® Elbow System", Biomet Orthopedics, Inc., (Nov. 30, 2007), 3 pgs.
"Discovery® Elbow System Surgical Technique", Biomet Orthopedics, Inc., (Dec. 31, 2008), 1-25.
"European Application Serial No. 07809326.7, Examination Notification Art. 94(3) dated Jan. 22, 2015", 6 pgs.
"European Application Serial No. 07809326.7, Extended European Search Report dated Nov. 15, 2011", 6 pgs.
"European Application Serial No. 09731923.0, Examination Notification Art. 94(3) dated Feb. 10, 2015", 7 pgs.
"European Application Serial No. 10705064.3, Examination Notification Art. 94(3) dated Feb. 4, 2015", 6 pgs.
"European Application Serial No. 12724475.4, Examination Notification Art. 94(3) dated Nov. 24, 2014", 7 pgs.
"Great Britain Application Serial No. 1116054.6, Search Report dated Dec. 21, 2011", 4 pgs.
"Hipsextant Instructions of Use", Surgical Planning Associates, Inc., (2011), 19 pgs.
"International Application Serial No. PCT/EP2010/061630, International Preliminary Report on Patentability dated Feb. 23, 2012", 13 pgs.
"International Application Serial No. PCT/EP2010/061630, International Search Report dated Nov. 30, 2010", 3 pgs.
"International Application Serial No. PCT/EP2010/061630, Written Opinion dated Nov. 30, 2010", 10 pgs.
"International Application Serial No. PCT/US2009/039507, International Preliminary Report on Patentability dated Oct. 28, 2010", 9 pgs.
"International Application Serial No. PCT/US2009/039507, Written Opinion dated Jul. 14, 2009", 7 pgs.
"International Application Serial No. PCT/US2009/039578, International Preliminary Report on Patentability dated Oct. 28, 2010", 9 pgs.
"International Application Serial No. PCT/US2009/039578, Written Opinion dated Jul. 31, 2009", 7 pgs.
"International Application Serial No. PCT/US2010/038177, International Preliminary Report on Patentability dated Dec. 22, 2011", 10 pgs.
"International Application Serial No. PCT/US2010/038177, Written Opinion dated Aug. 24, 2010", 8 pgs.
"International Application Serial No. PCT/US2010/038845, International Preliminary Report on Patentability dated Jan. 5, 2012", 9 pgs.
"International Application Serial No. PCT/US2010/038845, Written Opinion dated Jan. 5, 2012".
"International Application Serial No. PCT/US2011/026333, International Preliminary Report on Patentability dated Sep. 7, 2012", 10 pgs.
"International Application Serial No. PCT/US2012/026356, International Preliminary Report on Patentability dated Sep. 6, 2013", 8 pgs.
"International Application Serial No. PCT/US2012/026356, Written Opinion dated May 8, 2012", 6 pgs.
"International Application Serial No. PCT/US2012/038351, International Preliminary Report on Patentability dated Nov. 28, 2013", 9 pgs.
"International Application Serial No. PCT/US2012/038351, Written Opinion dated Jul. 6, 2012", 8 pgs.
"International Application Serial No. PCT/US2012/042081, International Preliminary Report on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 14 pgs.
"International Application Serial No. PCT/US2012/052853, Written Opinion dated Nov. 15, 2012", 12 pgs.

(56) References Cited

OTHER PUBLICATIONS

"International Application Serial No. PCT/US2012/059189, International Preliminary Report on Patentability dated Apr. 24, 2014", 10 pgs.

"International Application Serial No. PCT/US2012/059189, Written Opinion dated Dec. 18, 2012", 9 pgs.

"International Application Serial No. PCT/US2012/060842, International Preliminary Report on Patentability dated May 8, 2014", 7 pgs.

"International Application Serial No. PCT/US2012/060842, Written Opinion dated Feb. 6, 2013", 5 pgs.

"International Application Serial No. PCT/US2012/060848, International Preliminary Report on Patentability dated May 8, 2014", 11 pgs.

"International Application Serial No. PCT/US2012/060848, Written Opinion dated Apr. 12, 2013", 9 pgs.

"International Application Serial No. PCT/US2012/060853, International Preliminary Report on Patentability dated May 8, 2014", 11 pgs.

"International Application Serial No. PCT/US2012/060853, Written Opinion dated Apr. 9, 2013", 9 pgs.

"International Application Serial No. PCT/US2012/060854, International Preliminary Report on Patentability dated May 8, 2014", 8 pgs.

"International Application Serial No. PCT/US2012/060854, Written Opinion dated Feb. 6, 2013", 6 pgs.

"International Application Serial No. PCT/US2013/026875, International Preliminary Report on Patentability dated Sep. 4, 2014", 9 pgs.

"International Application Serial No. PCT/US2013/026875, Written Opinion dated Jun. 7, 2013", 8 pgs.

"International Application Serial No. PCT/US2013/057097, International Preliminary Report on Patentability dated Mar. 12, 2015", 10 pgs.

"International Application Serial No. PCT/US2013/057097, International Search Report dated Oct. 14, 2013", 6 pgs.

"International Application Serial No. PCT/US2013/057097, Written Opinion dated Oct. 14, 2013", 9 pgs.

"International Application Serial No. PCT/US2013/067505, International Search Report dated Apr. 14, 2014", 5 pgs.

"International Application Serial No. PCT/US2013/067505, Invitation to Pay Additional Fees dated Feb. 6, 2014", 6 pgs.

"International Application Serial No. PCT/US2013/067505, Written Opinion dated Apr. 14, 2014", 11 pgs.

"International Application Serial No. PCT/US2013/074288, International Search Report dated May 23, 2014", 7 pgs.

"International Application Serial No. PCT/US2013/074288, Written Opinion dated May 23, 2014", 11 pgs.

"International Application Serial No. PCT/US2014/022000, International Search Report dated Jun. 24, 2014", 3 pgs.

"International Application Serial No. PCT/US2014/022000, Written Opinion dated Jun. 24, 2014", 5 pgs.

"International Application Serial No. PCT/US2014/023655, International Search Report dated Jul. 10, 2014", 4 pgs.

"International Application Serial No. PCT/US2014/023655, Written Opinion dated Jul. 10, 2014", 6 pgs.

"Is Subchondroplasty® Right for Me?", [Online] retrieved from the internet: <http://www.subchondroplasty}..com/about subchondroplast}'./is subchondroplasty right for >, (Jul. 1, 2013), 1 pg.

"Japanese Application Serial No. 2014511538, Office Action dated Apr. 7, 2015", (W/ English Translation), 8 pgs.

"Knee tensor combined with laser femoral head locator", Research Disclosure, No. 507, (Jul. 2006), 903.

"Method for constructing an allograft sleeve", Research Disclosure, No. 476, (Dec. 2003), 1294.

"OSS™ Orthopaedic Salvage System, Femoral/Tibial Augmentation", Biomet Orthopedics, Inc.,, (Mar. 31, 2004), 1-8.

"Oxford® Partial Knee", Biomet, (Feb. 2011), 8 pgs.

"Oxford® Partial Knee Microplasty® Instrumentation Surgical Technique", Biomet, (May 2011), 1-54.

"Patient Matched PMI Implants, C.A.M.R.A. 3-D Imaging", Brochure, Biomet, Inc., Form Y-BMI-191/013191, (1991), 6 pgs.

"Regenerex® Tibial Cone Augment, Surgical Technique Addendum to the Vanguard® SSK Revision System", brochure. Biomet® Orthopedics., (Mar. 31, 2010), 1-8.

"Signature™ Hip Technology Personalized Patient Care brochure", Biomet® Orthopedics., (2013), 8 pgs.

"Signature™ Personalized Patient Care", Surgical Technique Acetabular Guide System brochure, Biomet® Orthopedics, (2013), 1-13.

"Signature™ Personalized Patient Care, Surgical Technique Addendum to the Vanguard Knee System", brochure. Biomet® Orthopedics, Inc., (May 15, 2009), 1-8.

"Signature™ Personalized Patient Care, Surgical Technique Addendum Vanguard® Complete Knee System", Biomet® Orthopedics Brochure, (2011), 1-32.

"Subchondroplasty", [Online] retrieved from the internet: <http://www.subchrondroplasty.com/>, (Jul. 1, 2013), 1 pg.

"The Oxford® Partial Knee Surgical Technique", Biomet, (Feb. 2010), 1-38.

"TruMatch™ Personalized knee replacement solutions", SIGMA® DePuy Orthopaedics, Inc, (2009), 2 pgs.

"Vanguard® PFR Partial Knee Patellofemoral Replacement System", Surgical Technique, Biomet Orthopaedics,, (Aug. 31, 2010), 1-25.

"What is Subchondroplasty", [Online]. Retrieved from the Internet: <http://www.subchondroplasty.com/about subchondroplasty/what is subchondroplasty.>, (Jul. 1, 2013), 2 pgs.

"Zimmer® UniSpacer® Knee System", Zimmer, Inc., (2005), 4 pgs.

Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.

Botha, Charl P, "Technical Report: DeVIDE—The Delft Visualisation and Image processing Development Environment", (May 31, 2006), 1-49.

Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.

Deakon, "Posterior Cruciate Ligament Reconstruction Technique Using the Modular ACL/PCL Guide Rationale and Surgical Technique", Arthrotek®, a Biomet Company, (2003), 6 pgs.

Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.

Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40, © Springer-Verlag London Limited, (2011), 9 pgs.

Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.

Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.

Friedman, R J, et al., "The Use of Computerized Tomography in the Measurement of Glenoid Version", Journal of Bone & Joint Surgery Am. (JBJS) 1992;74, (Aug. 1992), 1032-1037.

Haaker, R G, et al., "Minimal-invasive navigiert implantierte unikondylare Knieendoprothese", Orthopade 2006 35: Spinger Medizin Verlag, (Sep. 13, 2006), 1073-1079.

Hafez, M A, et al., "Computer-assisted Total Knee Arthroplasty Using Patient-specific Templating", Clinical Orthopaedics and Related Research, No. 444 Lippincott Williams & Wilkins, (2006), 184-192.

Hazan, Eric J, "Computer-Assisted Orthopaedic Surgery, A New Paradigm", Techniques in Orthopaedics® vol. 18, No. 2,, (2003), 221-229.

(56) References Cited

OTHER PUBLICATIONS

Hutmacher, Dietmar W, "Scaffolds in tissue engineering bone and cartilage", Biomaterials, 2000 Elsevier Science Ltd., (2000), 2529-2543.

Kaus, Michael R, "Automated Segmentation of MR Images of Brain Tumors", Radiology, vol. 218, No. 2,, (2001), 586-591.

Kelly, Todd C, "Role of Navigation in Total Hip Arthroplasty", The Journal of Bone & Joint Surgery(2009) vol. 91-A, Supplement 1, (2009), 153-8.

Klein, M, "Robot assisted insertion of craniofacial implants—clinical experience", CARS 2001, Elsevier Science B.V., (2001), 133-138.

Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.

Lynch, John A, et al., "Cartilage segmentation of 3D MRI scans of the osteoarthritic knee combining user knowledge and active contours", Medical Imaging 2000: Image Processing SPIE vol. 3979, (2000), 925-935.

Murphy, S B, et al., "The Hip Sextant: Navigation of Acetabular Component Orientation Using a Mechanical Instrument", (2009), 1 pg.

Nicholls, Paul M. D, "Trauma Grand Rounds PMI (Patient-Matched Implants)", Biomet Orthopedics, Inc.,, (Feb. 29, 2000), 1 pg.

Overhoff, H M, et al., "Total Knee Arthroplasty: Coordinate System Definition and Planning based on 3-D Ultrasound Image Volumes", CARS 2001, Elsevier Science B.V., (2001), 283-288.

Portheine, F, "CT-basierte Planung und DISOS-Schablonennavigation in der Kniegelenkendoprothetik", Navigation und Robotic in der Gelenk—und Wirbelsaulenchiruqie, Kapitel 32, Springer Verlag, (2003), 262-269.

Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.

Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.

Radermacher, K, et al., "Computer Integrated Orthopaedic Surgery: Connection of Planning and Execution in Surgical Intervention", Computer-integrated surgery: technology and clinical applications, (1996), 451-463.

Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.

Radermacher, K, et al., "Image Guided Orthopedic Surgery Using Individual Templates", Springer Berlin/Heidelberg, CVRMed-MRCAS'97, vol. 1205, (1997), 606-615.

Radermacher, K, et al., "Technique for Better Execution of CT Scan Planned Orthopedic Surgery on Bone Structures", British Library—"The world's knowledge" 2nd Congress of ISCAS Conference, (Jun. 1995), 933-938.

Radermacher, Klaus, et al., "Computer Assisted Orthopaedic Individual Templates", Clinical Orthopaedics and Related Research No. 354, (Sep. 1998), 28-38.

Radermacher, Klaus, et al., "Computer Assisted Orthopaedic Surgery with Image Based Individual Templates", Clinical Orthopaedics and Related Research No. 354, Lippincott Williams & Wilkins, (Sep. 1998), 28-38.

Schuller-Gotzburg, P, et al., "3D-Implantatplanung and Stereolithographie-Implantatbohrschablonen", Stomatologie 101.3, (May 2004), 55-59.

Sharp, Michael S, "Patient-Specific, Resurfacing Bi-Compartmental Arthuroplasty Futuretech", Orthopaedic Product News, (Apr. 2008), 12-15.

Sisto, Domenick J, et al., "Custom Patellofemoral Arthroplasty of the Knee Surgical Technique", Journal of Bone and Joint Surgery, vol. 89-A, (2006), 214-225.

Slamin, John, et al., "Do You Have This Implant in My Size?", MDT Medical Design Technology, [Online]. Retrieved from the Internet: <http://www.mdtmag.com/scripts/ShowPR.asp-?PUBCODE=046&ACCT=0007796& ISSUE . . . >, (Jul. 31, 2008), 3 pgs.

Steinwachs, Matthias Reinhard, "Cartilage Repair—Autologous Chondrocyte Transplantation and Autologous Matrix-induced Chondrogenesis", European Musculoskeletal Review, (2006), 65-68.

Thoma, W, et al., "Endoprothetischen Versorgung des Kniegelenks auf der Basis eines 3D-computertomographischen Subtraktionsverfahrens", Topic: Computer-aided orthopedic surgery. Orthopedist 2000 29: Springer Verlag W/ Original German Document, (2000), 641-644.

\* cited by examiner

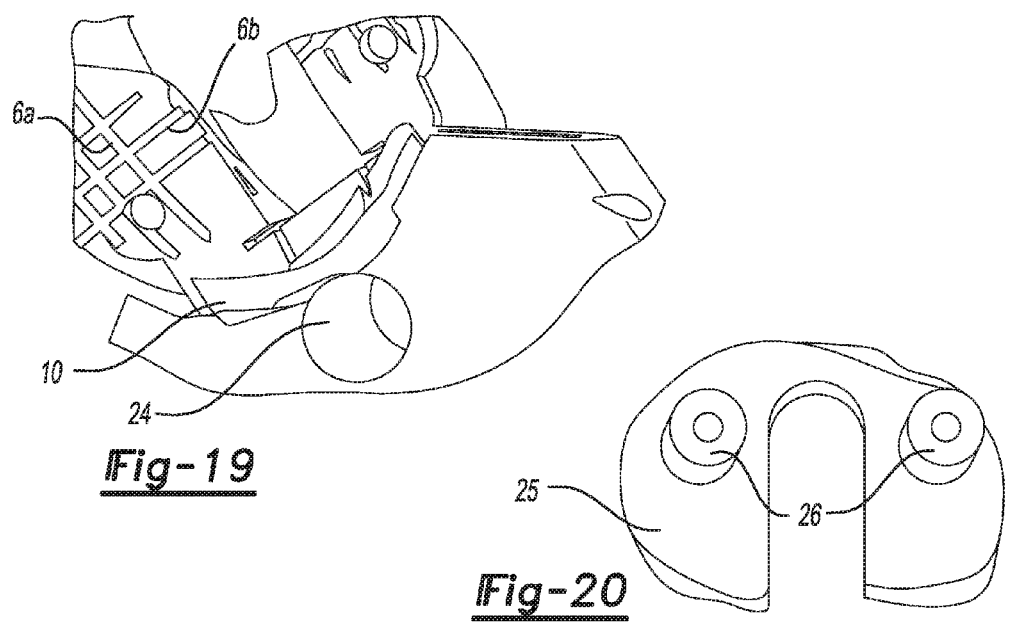
Fig-19
Fig-20
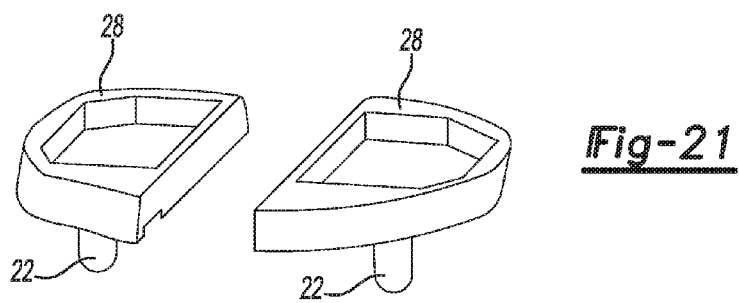
Fig-21
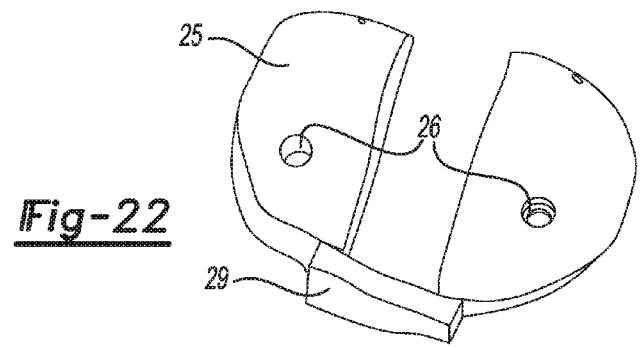
Fig-22

DEVICE FOR THE RESECTION OF BONES, METHOD FOR PRODUCING SUCH A DEVICE, ENDOPROSTHESIS SUITED FOR THIS PURPOSE AND METHOD FOR PRODUCING SUCH AN ENDOPROSTHESIS

CROSS-REFERENCE TO RELATED APPLICATIONS

This application is a continuation of U.S. patent application Ser. No. 13/389,700 filed on Apr. 30, 2012, which is a U.S. National Stage Application of International Application No. PCT/EP2010/061630 filed on Aug. 10, 2010 and published in German as WO/2011/018458 on Feb. 17, 2011. This application claims the benefit of German Application No. 10 2009 028503.2, filed on Aug. 13, 2009. The entire disclosures of the above applications are incorporated herein by reference.

The present invention relates to a device for resection of bone, particularly to the preparation of the mounting of an endoprosthesis, a method for manufacturing such a device, an appropriate endoprosthesis, a method for manufacturing such an endoprosthesis and a surgery set, consisting of these components, and which is particularly suitable for performing knee joint surgery. Such devices present tool guide, for example for wielding a scalpel for resection of a bone as well as supports, which position and adjust the tool guide relatively to the bone.

According to slate of the art, it has been well known for many years to work with templates as implantation aid, for example with traditional knee joint surgeries, whereas generally, these templates consist of metal and are assembled from a wide range of instruments and scalpel apparatus which are very complex and delicate in some cases, and which require a multitude of adjustments and measuring steps during surgery in order to achieve a precise adjustment of tool guide, such as scalpel guidance, for ensuring the exact resection of the bone and for maintaining the proper fit of the prosthesis. Generally, the surgeon must go through extensive training, and during surgery, he has to perform a multitude of strenuous adjustment and measuring procedures under the highest level of concentration.

For example, under DE 4 434 539 C2 methods have been described by which an image of the damaged bone, such as a damaged knee joint, is made before the actual surgery by using computer tomography or magnetic resonance imaging. These pre-operative images could be adjusted accordingly, while conducting an approximation of the contours of the damaged bone to the contours of a healthy bone. After such a correction, a virtual post-operative image of the damaged bone is made, which offers a direct comparison with the pre-operative image. From this comparison, a subtraction image is made which allows the manufacturing of the endoprosthesis. With it, the natural contour of the bone is approximated as precisely as possible.

From EP 1 074 229 A2, it is known to separate the damaged bone areas virtually with the help of a tomographic image, first of all, in which the separation is made on marked cut surfaces. As a result, pictorial models are obtained which are proximately oriented on the damaged bone, and can be virtually completed with the help of a healthy bone structure, where applicable, and then, they can be used for the manufacturing of an endoprosthesis which is precisely adapted to the cut surfaces and the natural bone structure. Simultaneously, these pictorial models are used for the manufacturing of an implantation aid, which means that the cut surfaces are included in a template which is adapted to the individual bone structure of the patient. These implantation aids can be used for the implantation of individual endoprostheses according to EP1 074 229 A2 as well as conventional, standardized and non-individually or only partly individually adjusted prosthesis.

From DE 42 19 939 A1, a template for appropriate tools for the modification of bony structures and a method defining the correlation of these tools to these bony structures are known, whereas first of all, only sectional images of the bony structure are made and a three-dimensional design of this structure and its surface is obtained. Subsequently, in the pre-operative planning stage, an individual template is manufactured which rebuilds the surface of the bone structure and will be applied to the exposed points of contact and contact areas in order to guarantee a defined tool guide during surgery.

State-of-the-art templates and implantation aids which have been manufactured with the help of tomographic pictorial models and which feature tool guide, such as cutting edges and cutting cores as well as areas adapted to the bone structure for attaching the templates, partially have the disadvantage of a necessary adaption of the templates during surgery by additional extensive measurements of bone axes and ligament tensions or of a precise adaption only being possible with a marking which had been attached to the bone pre-operatively. The reason for this is that the precise surface structure of the bones cannot be exactly determined in virtual environments due to physical limits at image taking, for example because of soft tissues or bulges which cannot be exactly defined in the images, contact-areas are over-determined and oversized areas are included which cause an extensive arithmetical and partly manual effort at establishing data records as well as a template that cannot be adapted precisely and is loose. Therefore, most often it is necessary to pre-operatively attach appropriate pins or wires to the bone before three-dimensional pictures are taken. Afterwards, the template will be attached to them.

By using such an individual template, the adjustment and measuring procedures are shifted before surgery, even without the use of markers or pins. The templates are completed according to an image previously obtained by computer tomography, for example of the knee joint skeleton, in order for the guide cores of the saw blades to guarantee the ideal resection areas for the prosthesis bed. After opening of the surgical site, precast templates will be positioned on the bone and enable an immediate resection of bone which provides a significant relieve for the surgeon who can thus focus on other important details of surgery, such as operational access, hemostasis and soft tissue management. As a result, the implantation can be carried out in a more precise, secure and safe way than by use of conventional, reusable and partly adapted individually implantation aids or templates as described in the above mentioned publications.

Another disadvantage of the conventional implantation technique is the high expenditure of time needed for conduction the adjustment procedures during surgery which requires keeping the surgical wound open for longer and increases the risk of infection. Additionally, the so-called tourniquet prevents the blood circulation of the extremities during surgery and damages soft tissue with increasing duration of surgery. Not least, this results in a prolonged anaesthesia time for the patient and thus, an increased risk of surgery for thromboses, embolisms and cardiopulmonary complications, among other things.

Implantations performed with the required technique according to EP 1 074 229 B1 reduce the required surgery time, on average by well above half of the usual surgery time, on average, and put less strain on the patient. Furthermore, reusable, non-individually adapted implantation instruments have the disadvantage of a more extensive production, storage, maintenance and sterilization compared to individually produced single-way- or one-way-articles. Individual templates can be manufactured from plastics, such as polyamide, as one-way-articles whereas although production costs occur with each surgical intervention, their manufacture is increasingly cost-effective and faster due to today's computer-assisted three-dimensional manufacturing techniques (such as "rapid manufacturing"). Furthermore, no costs for cleaning, sterilizing, storage, maintenance and controlling occur. Nevertheless, the disadvantage of the individually adapted templates is that they cannot always be manufactured pre-operatively in such a precise way in order for the support, which generally consists of surface of the template which is negatively shaped to the bone surface, to capture the bone surface exactly.

In the images taken pre-operatively, cartilage tissue, fibro-cartilage or bone tissue cannot be clearly identified to some extent which creates the possibility of a moving of the template upon applying on the bone and as a result, the tool guide is not found precisely in place where the bone needs to be prepared.

In the treatment of patients with knee joint endoprosthesis, the use of templates individually attached to the bone, as described in EP 1 074 229 B1 or DE 42 19 939 A1, results in a shifting of the adjustment and measurement procedures from the operating theaters and hence, to a simplification of the surgery and a reduction of surgery time.

While this state-of-the-art technology fully describes the possibility of a precise resection of bone and while a remark in these prints can be found which states that it opens the possibility of an extensive preservation of the ligaments of the knee joints and accordingly a better adaption of the ligamentous structures of the knee joints, the generally still necessary corrections of the ligamentous tension on the knee joint (soft tissue alignment) has not been mentioned in this connection because the use of conventional individual implementation aids does not provide relieve or benefits in the first place.

Generally, with the further advance of the arthritis of the knee joint in addition to the changes of the joint surfaces, a corresponding transformation in the ligamentous structures takes place. In most places, by inflammation a slight shrinkage or reduction of the ligaments is caused, occasionally also a loosening in connection with a mechanical overwork takes place.

The most common instance of an arthrosis which primarily takes place in the internal compartment of the knee joints leads to an impairment or even destruction of the cartilage lining, predominantly of the internal tibia area and the internal femoral condyle with simultaneous shortening of the ligamentous structures of the internal and rearward capsular ligament apparatus. Because of the slight bow-leg deformities that are often connected with it, an increased tension on the outer ligamentous apparatus continues along with it which occasionally loosens or changes slightly due to chronic, mechanical overload.

With a surgical replacement of the knee joint by a knee joint endoprosthesis, it is necessary to optimally reconstruct the mechanical leg axis as well as to adjust the ligamentous tension as precisely as possible in order to prevent an incarnation on one side and an instability on the other side. This has to be achieved in the extension position as well as the flexion position of the knee joints.

The conventional methods, as for example, mention in the implantation description "Aesculap Orthopaedics Columbus, knee endoprosthesis system"; prospectus no. O254 01 by the company Aesculap AG, are limited to determining the mechanical axes precisely and performing the resection on the femur as well as on the tibia in order to straighten the joint line horizontally in the frontal plane, with a contingent undefined, slight backward drop (slope) in the lateral plane and subsequently, the ligamentous apparatus of the implanted prosthesis is adjusted in extension position and flexed position to this situation.

However, this method does not consider the joint line of the patient which plays an important role in terms of exact height, backwards tilting and the occasional lateral inward tilting, according to latest findings.

Since this newly created joint line causes a complete change of the kinematic interaction of the joint surface and the ligaments, it is often necessary to adapt the ligamentous tension for the stretching position and/or the flexing position while at the same time, not only the short ligament structures but also the healthy structures frequently have to be corrected and the anterior cruciate ligament is regularly and the posterior cruciate ligament is often removed. In many cases, the entire biomechanics experience a fundamental change which is an area of concern, especially in the interaction with the knee joint and which can be quite painful for the patient after surgery.

At least, the implantation method according to EP 1 074 229 B1 takes the patient-specific joint line into account, but here, too, the individual adapted knee joint endoprosthesis is too tight internally and accordingly, the ligamentous apparatus is shortened and tightened after a correction of the height defect of the tibia area and the femoral condyle cause by arthrosis and mostly due to cartilage damage which makes a correction of the ligamentous tension necessary but only in the area of the abnormal capsule tissue.

In the more rare cases where the outward capsule apparatus is loosened by excessive mechanical demands, a slight overcorrection of the inward ligamentous apparatus is necessary; with a simultaneous increase of the tibia area (for this purpose, three tibia plateau heights with 1 mm height increase each compared to the original height respectively the height "plus one" are provided).

By this method, the repeated measuring and the repeated insertion and testing of the prosthesis or of a trial implant are necessary, too. This will be carried out by—as with other conventional implementation methods—first implanting the thigh component or lower leg component (femoral or tibial component) as cost-**effectively as possible, depending on the method (femur first or tibia first), and subsequently implementing the resection for the second component by taking into account the leg axis and the adjustment of the capsule ligament apparatus at extension and diffraction.

The function of the invention is the specification of an appropriate device which simplifies the surgical procedure for the surgeon, minimizes the risk of error, shortens the length of surgery, minimizes costs and guarantees an exact adaption of the tool guide without the need of extensive readjustment and, at the same time, makes allowances for the aforementioned, individual biomechanics of the patient.

Another function of the present innovation is the implementation of a method for the manufacture of such a device as well as appropriate endoprostheses and methods for the manufacture of such endoprostheses.

These problems are solved by distinguishing features of the independent patent claims 1, 10, 13, 15 and 17. Advantageous definitions of the present invention are identified in the subclaims and described there. Especially preferred embodiments of the present invention for the treatment of knee joints, that is to say the tibia bone and the femur bone, are explained by use of the enclosed images.

The inventive device for the resection of bones for the preparation of an attachment of an endoprosthesis to the joints which consists of at least two jointly cooperating joint parts features at least one tool guide and at least one support appropriate for adapting for at least one tool guide whereas the support enables either the cross joint adjustment and positioning of at least one tool guide at one further joint part or distally to the area which needs to be prepared, and resected in particular, and/or the adjustment and positioning of at least one tool guide on the same joint part outside the surgical area.

Outside the surgical area, the support according to a preferred embodiment can also take place on intact skin-soft tissue surfaces on the same or the opposite joint part. Within the surgical area, a support takes place preferentially on the bone in immediate vicinity of the bone which needs to be resected on the same or the opposite joint part.

According to the invention after the resection of, for example, the thigh bone for the implantation of an endoprosthesis thigh component, for example, by use of an initial individual thigh bone template, first of all, the support—in the form of a second template—is attached on, for example, the thigh bone will need to be resected and prepared. According to a preferred embodiment of the present invention, this inventive support consists of a 3-dimensional-restruction of the thigh prosthesis components which needs to be implanted, made of, for example, polyamide. The resection device and accordingly the tool guide for the resection on the lower leg bone adheres firmly to this inventive support, that is to say, the thigh prosthesis component, for the manufacture of an implant bed for the lower leg bone component.

With the known height of the necessary endoprosthesis tibia components (tibia plateau), the distance between the underpart of the thigh prosthesis components reconstruction and the cutting area, determined with the help of this tool guide, correspond exactly to the height of the endoprosthesis tibia components, so that a resection on the tibia bone which suits this prosthesis component perfectly is guaranteed, in any case.

With the help of so called distractors, such innovative templates enable an exact examination of the ligamentous tension before resection as well as during extension and diffraction. For this purpose appropriate slots are attached to the the joint area remote to the body (distal) and to the backward (dorsal) joint area of the prosthesis components of the template. Here, the ligamentous tension can be controlled and corrected with the adjoining template and without removing it repeatedly regarding extension as well as diffraction.

However, it is important to consider that on the thigh prosthesis component reconstruction of the template, that is to say the inventive support, the cartilaginous defect has already been corrected but the cartilaginous defect on the lower leg side is still existing because there, the original bone of the patient is still present and as a result the height defect of the tibia plateau needs to be corrected initially by introducing an appropriate placeholder until it is compensated by the replacement with the tibia component of the endoprosthesis.

The height of the defect and accordingly the height for this placeholder is determined pre-operatively by means of the height difference between the actual height of the patient's tibia plateau and and the height of the tibia plateau of the tibia component which is approximately identically to the height of a healthy knee joint. This corrective measure can also be achieved by a correspondingly higher adjustment of the distractors to the height of the cartilaginous defect which makes the use of a placeholder unnecessary.

The leg axis can be continuously monitored by inserting a measuring stick into the openings or this inventive device or template provided for this purpose. If the leg axis is adjusted correctly and the ligamentous tension is sufficiently balanced in extension as well as diffraction, the lower part of the template with the tool guide can be secured to the tibia by introduction of the so called Kirschner's wire into the appropriate canals, and the resection can be done securely on the determined area of the lower leg bone.

This cross-jointed adjustment and resection of each of the opposite joint parts enable a simpler, more reliable and faster performance of this surgical step in comparison to the state-of-the-art techniques.

Occasionally, very contracted and tight ligaments are present with arthrotic knee joints which make it very difficult to adjust an appropriate template to the joint without conducting extensive soft tissue solutions and therefore, causing damages to it. In these cases, the reverse procedure is suggested (tibia first) where the tibia is resected initially in order to provide enough space in the joint. The tibia resection takes place according to the invention by use of a support which is distal to the area which needs to be resected and/or enables the adjustment and positioning of at least one tool guide on the same joint part, thus, the tibia, outside the surgical area.

This inventive support enables a bony support, such as on the surgically opened tibial plateau by, for example, a sleeve-shaped support to the skin and the skin of the bone over the intact, distal shinbone. Thereby, a precise positioning of the template with regard to the tibial axis as well is provided.

To be specific, a major problem the precise positioning of the individually adapted tibia template. Different from the thigh bone, the tibia area cannot be exposed so far that it can be partly covered with a template. Additionally, on the tibia, there are less so called "landmarks" where the template can be adjusted securely. Even the smallest tilting can cause serious deviations from the planned resection line.

With the template system used so far, only a bony support on the dissected tibia bone in the immediate vicinity of the tibia plateau—in case it can be uncovered—is used by employing, for example, punctual or linear supports (DE 42 19 939 A1).

Figure 11:
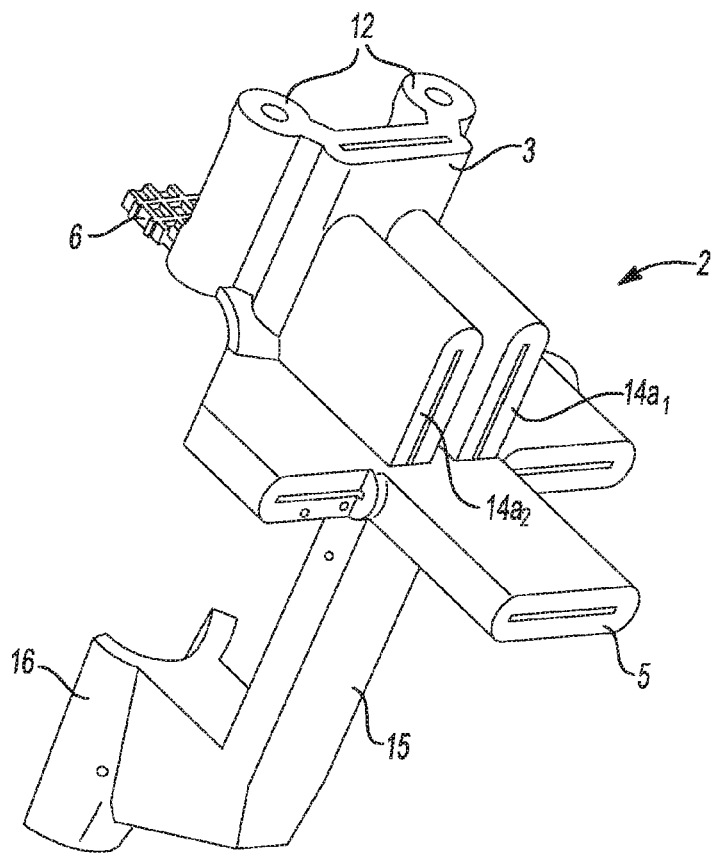

With the combination of a bony support on the tibia plateau—if it can be dissected that far—and a support outside the surgical situs, on the lower part of the tibia, with a support on skin and skin of the bone of the tibia which sit directly on the bone in this part of the body and therefore, similar to exposed bones, provide a good counterfort for templates, such as shown in FIG. 11, an adequately secure and precise positioning of the template and its cutting areas in the angles individually needed can be achieved due to the relatively long lever-arm between the bone-supported template and the shinbone positioned far below.

This adjustment of a tibia template in immediate vicinity of the joint on the which has not yet been practiced according to state-of-the-art techniques in immediate vicinity of the joint on the dissected bone and, at the same time, on the distal, far-flung tibia covered with a thin skin of the bone and skin layer, outside the surgical area, increases the precision and reliability of the positioning of the template and the bone cutting significantly.

When implanting knee joint total endoprosthesis, incorrect positioning with small mistakes regarding diffraction or extension are tolerated relatively well, therefore, only little attention has been paid to the adjustment of diffraction and extension. Within the scope of increasing demands on implantation accuracy, especially regarding individually adapted endoprostheses and the preservation of cruciate ligaments, such a device for controlling and correction is increasingly gaining in importance.

The described methods for an axially adjustment of the components of the prosthesis as well as for the exact adjustment of the ligamentous tension can be implemented—with slight variations and in different combinations with the following—with features, as described in detail below, with conventional and also individually manufactured bicondylar and monocondylar knee joint endoprostheses. Furthermore, such templates can be applied for the implementation of revision endoprostheses and tumor prostheses. These preferred features will be explained further:

The inventive device for the resection of bones, especially for the preparation of adapting an endoprosthesis, preferably shows at least another support suitable for adaption of at least one tool guide whereas the support is designed punctual or linear. At the same time it is preferred that at least one of the tool guides as well as at least one of the support devices is connected immovably, so that a resection master plate is created from tool guide and the at least a punctual or linear support device. Punctual for the purpose of this device means that small areas are affected which amount to less that 10% of the complete area each, preferably less than 5% of the complete area, especially preferred between 0.1% and 3% of the complete area as area for supporting the bone or cartilage.

The tool guide and the support can each be manufactured as a separate component of the resection template, which can be immovably connected at the support by fastening devices like screws, braces or locks according to the adaption method which has been determined before surgery. In this connection, the tool guide can be manufactured from a more consistent, for example, a vitrifiable metallic material in series, for example, in five different sizes and then, be connected and adjusted repeatedly with different, unmodified individually manufactured supports from plastics, for example, polyamide. This saves production cost.

The use of the "rapid manufacturing"-technology makes it possible to manufacture individual resection templates which can be made under use of, for instance, computer tomographic data instead of a wide variety of standardized metal templates which can not be adjusted to the patient's bone until the actual surgery is performed. For example, two resection templates for the treatment of a knee joint—one for the femur and one for the tibia—can be produced from, for example, polyamide, polyurethane, epoxy resin or suchlike, which means from a suitable and sterilized material appropriate for the "rapid manufacturing"-technology.

For this purpose, the punctual or linear support is molded according to two- or three-dimensional images of the bone which needs to he treated, such as tomographic images, whereas the linear shape of the support is molded along defined surface structures of the bone or rather, the punctual shape of the support is molded according to special surface areas of the bone according to two- or three-dimensional images. At the same time, one or several tool guides can also be positioned and adapted relatively to the surface structure of the bone according to the two- or three-dimensional image data so that a three-dimensional data record is gained which can be used for the manufacturing of templates.

According to a special embodiment of the present invention, several initial linear supports in several initial—basically parallel—levels are kept from each other at a distance and several second linear supports in several second—basically parallel—levels are kept from each other at a distance, whereas several initial and several second levels are not arrayed parallel to each other but basically rectangular to each other, so that a grid-shaped surface structure or supporting structure results from it which supports the template and accordingly the implantation aid with the help of the bone during surgery. For this purpose, two-dimensional computer-tomographic images are appropriate which make it possible to recognize the exact contour of the bone in the cross section area. Precisely, these sectional images are implemented as linear supports inside the template so that cavities between the linear or the punctual supports are worked into the templates, in which existing (not recognized) cartilage tissue, for example, fibrous cartilage or bone tissue can spread without disturbing the adjustment of the template and its adaption.

The rib construction at manufacturing of the linear supports has the advantage that only precise landmarks of the bone are shown and worked into the template whereas the effort of the reconstruction of the joint surface negative is not only reduced but an exact and precise support on the bone is guaranteed. Additionally, according to a special embodiment of the invention, the ribs can show an elasticity which compensates possible inaccuracies of the surface depending on the material used and the chosen rib thickness. Because of their elasticity, the ribs can be pushed aside by cartilages or soft tissue elevations not shown in the images whereas the position of the template is clearly held in the right position by the mainly correctly resting rib sections. On clearly and easy to define areas of the bone and cartilage surface, the rips can additionally be strengthened, for example, by additional vertical rib tractions which are not parallel to the initial ones.

According to another embodiment of the present invention, at least one tool guide features a guidance depth which basically extends between the bone and the guide stops of the tool guide which means, in the case of a cutting core, this would be the depth of the core of the template so that an exact depth of resection according to a pre-defined immersion depth of the tool is guaranteed. The guidance depth and the depth of resection account for the immersion depth of the tool, which is the depth of the template and the bone into the tool immerses. Because of the guide stop on the distal end of the tool guide, a precise immersion depth of the tool and thus, a pre-defined depth of resection and processing depth is given.

The several grid-shaped, especially linear supports and the several tool guides which are angular to each other preferably build a resection template which can be advantageously molded from a cast or worked from a material in such a way that the template is seamlessly formed from one piece. For the molding of the template, the aforementioned three-dimensional image data is appropriate which is complemented correspondingly by the tool guides and the working areas on the bone. Therefore, the template which is individually adjusted to the bone does not only guarantee a precise adaption of of each tool guide in relation to each other, but also an exact positioning of the tool guide on the bone so that the separately manufactured endoprosthesis does not only fit exactly to the cut surface after resection but also approximate precisely the original natural and healthy structure of the bone, especially its surface.

With this advantage, the template additionally has viewing openings or fixation openings in order to enable the surgeon the sight into the surgical area during surgery or rather to additionally fix the template to the bone, for example, in case the tool is used and a movement of the template is suspected. Through these fixation openings, for example, screws, nails or wires can be inserted into the bone for the adjustment of templates, whereas it is not necessary to define corresponding marking areas on the bone because the exact positioning of the template on the bone is already guaranteed by linear or punctual supports.

According to another embodiment of the invention, the template can also display other supporting areas or supports which can he connected to other body parts which take up a steady and immovable position towards the bone which needs to be prepared.

The inventive method for manufacturing a device for the resection of bones with at least one tool guide and at least one support appropriate for adapting at least one tool guide preferably displays the following steps:

1. Two- or three-dimensional images of the bone which needs to be prepared on are taken or made. For this, radiographs or resonance images are appropriate which show the bone which needs to be prepared on in layers.
2. Subsequently, punctual and/or linear contours of the bone are recognized in the two- or three-dimensional images. Suitable are state-of-the-art rendering methods which automatically scan and detect such contours due to shades of gray values.
3. Subsequently, the suitable tool guide is selected and positioned by means of two- or three-dimensional images. The positioning is conducted by means of determining the area which needs to be prepared, so for example, it is determined at which edge of the bone an area needs to be cut off. For this purpose, a cut surface is defined for which a tool guide for guiding a saw is positioned.
4. Finally, the template is manufactured with at least one support which enables the adjustment and positioning of at least one tool guide to another joint part in immediate vicinity of the joint or cross jointed or enables the adjustment and positioning of at least one tool guide to the same joint part distal to the area which needs to be resected and/or outside the surgical area. For this reason, at least one tool guide is manufactured which is positioned and adjusted relatively to the support. Suitable methods are the known "rapid manufacturing"-technologies, in which the template can be molded or formed from a suitable plastic or polymer blocks are worked on with appropriate milling, cutting or drilling machines or a combination of the aforementioned methods is used. This is recognized as state-of-the-art technology.

For the production of a template, a three-dimensional data record is used, which includes the punctual and linear supports for the attachment of the templates to the bone. The linear shape of the support occurs preferably along defined surface structures of the bones and the pointed shape occurs according to special area features of the bone which can be detected with the help of two- and/or three-dimensional images.

According to a special embodiment of the present innovation, several grid-shaped, linear supports and several tool guides which are angular to each other are determined with the help of two- and/or three-dimensional images, and subsequently, saved in a three-dimensional data record for the manufacturing of an inventive template. For the seamless manufacturing of the template, the supports and tool guides are molded according to the three-dimensional data record.

After another preferred configuration of the present invention, the template can be configured universally adjustable. For this purpose, the template or the device is initially manufactured as described above, preferably from stainless steel and instead of rips, contact plates on different, for example, nine different points of the femur, are adjusted which are adapted to the precise distance before the surgery by, for example, bolt threads and which are locked in this position by an appropriate locking screw. The adjustment of the point-shaped support takes place in vitro, with the help of two- or three-dimensional images. Therefore, an adjustment during surgery is not necessary anymore but can still me made, if desired. In terms of this invention, "immovable" relates to the tool guides and the supports.

If necessary, some screws need to be removed before bringing in the saw blades into the resection cores, because in this area, an intersection of resection core and bolt thread can possibly not be avoided. Reusable femur and tibia templates and femoral tibia templates are preferably kept ready in, for example, five different sizes in order to satisfy the individual needs of the patient regarding height differences. The reusable templates as well as the traditional surgical instruments are cleaned, sterilized and reused.

Furthermore, according to another embodiment of the present invention, devices for the attachment of sensors, such as a customary navigation system (for example Orthopilot® of the company Aesculap AG), can be fixed to the template and with its help, the focus point of the femoral head can be determined kinematically. With its help, the tibial axis can be adjusted, for example, mechanically and/or with the help of a navigation system as well.

The present invention also applies to a method for the manufacturing of an endoprosthesis for attaching to a bone which has been especially prepared with one of the aforementioned devices. The following procedural steps are appropriate:

1. Two- or three-dimensional images of the bone which needs to be prepared are taken or already prepared two- or three dimensional image data is used for the manufacturing of a device for the resection of bone.
2. Subsequently, the areas of the bone which need to be prepared are determined and the area which needs to be removed from the bone is chosen and positioned.
3. Afterwards, a virtual correction of the two- or three-dimensional images or the respective image data is carried out in order to achieve an approximation of the contours of the bone or the cartilage to the contours of a healthy bone or cartilage. Thus, the image data is completed or changed in order to achieve an "ideal bone or cartilage."
4. Subsequently, an inventive template for the resection of bone for the preparation of attaching an endoprosthesis to the joints is manufactured which consists of at least two jointly cooperating joint parts whereas the template is equipped with at least one tool guide and at least one support which is appropriate for the adjustment of at least one tool guide whereas the support enables either a cross joint adjustment and positioning of at least one tool guide on another joint part or enables the adjustment and positioning of at least one tool guide to the same joint part distal to the area which needs to be resected and/or outside the surgical area.

5. Finally, the endoprosthesis is manufactured according to the areas of the bone or cartilage which need to be prepared and the virtual correction of the two- or three-dimensional image data. In particular, the endoprosthesis is adapted molded according to the cut surfaces of the bone or cartilage as well as the outer contour of the healthy bone or cartilage.

The virtual correction of the two- or three-dimensional image of the damaged bone or cartilage is carried out by a comparison with images of healthy bones or cartilage which show shapes similar to the damaged bones or cartilage. Alternatively, a virtual correction can be conducted with the help of an interpolation of the healthy shapes of the bones/cartilage.

The present invention also applies to an endoprosthesis which has been manufactured with the aforementioned method and, in particular, is adjusted to a bone/cartilage which has been prepared with one of the aforementioned devices. Alternatively, the endoprosthesis can be connected immovably with an inventive device in order to serve as supporting surface area for the positioning of the template.

Ultimately, the present invention also applies to a surgery set for conducting knee joint surgeries consisting of femoral and/or tibial components of an endoprosthesis or femoral and/or tibial components of a device, that is, a template or implantation aid as described more precisely above.

Figure 2:
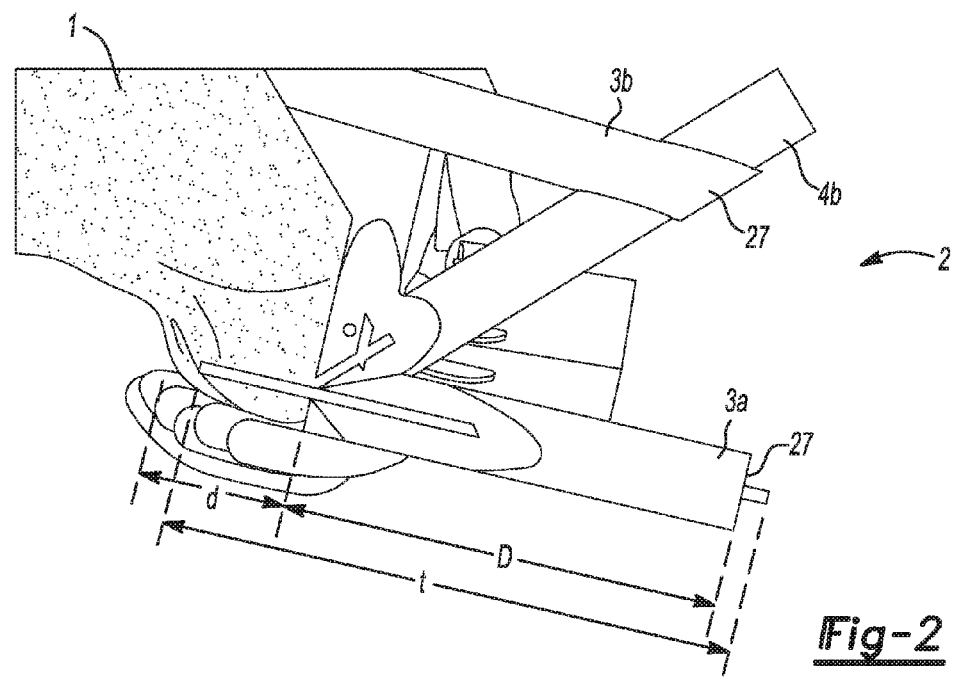
Figure 3:
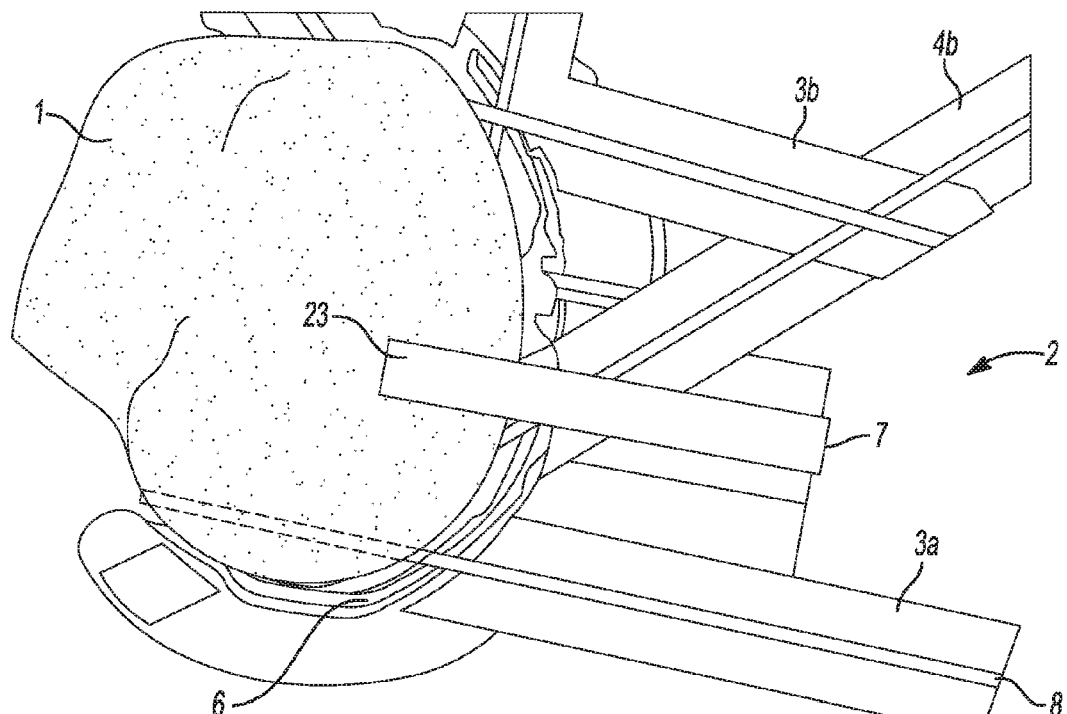
Figure 4:
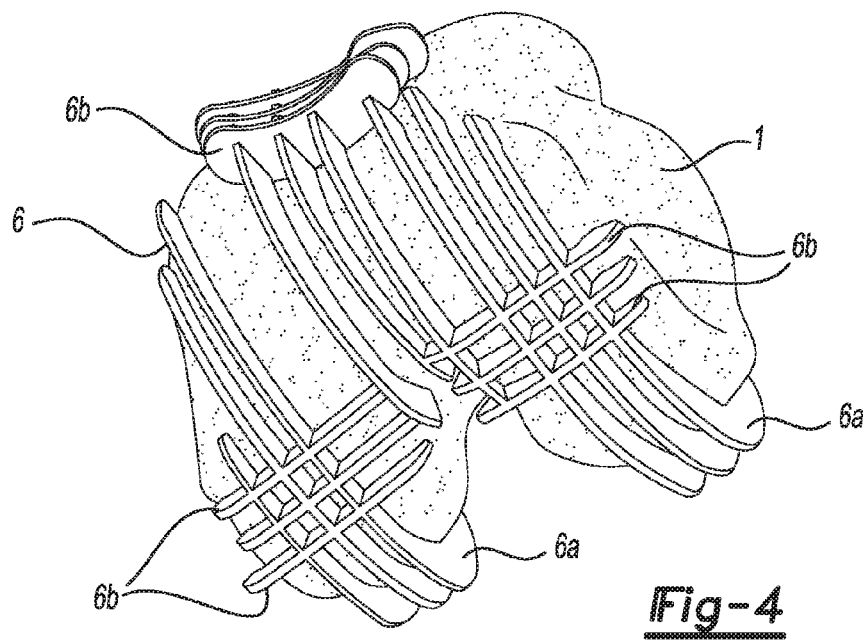
Figure 5:
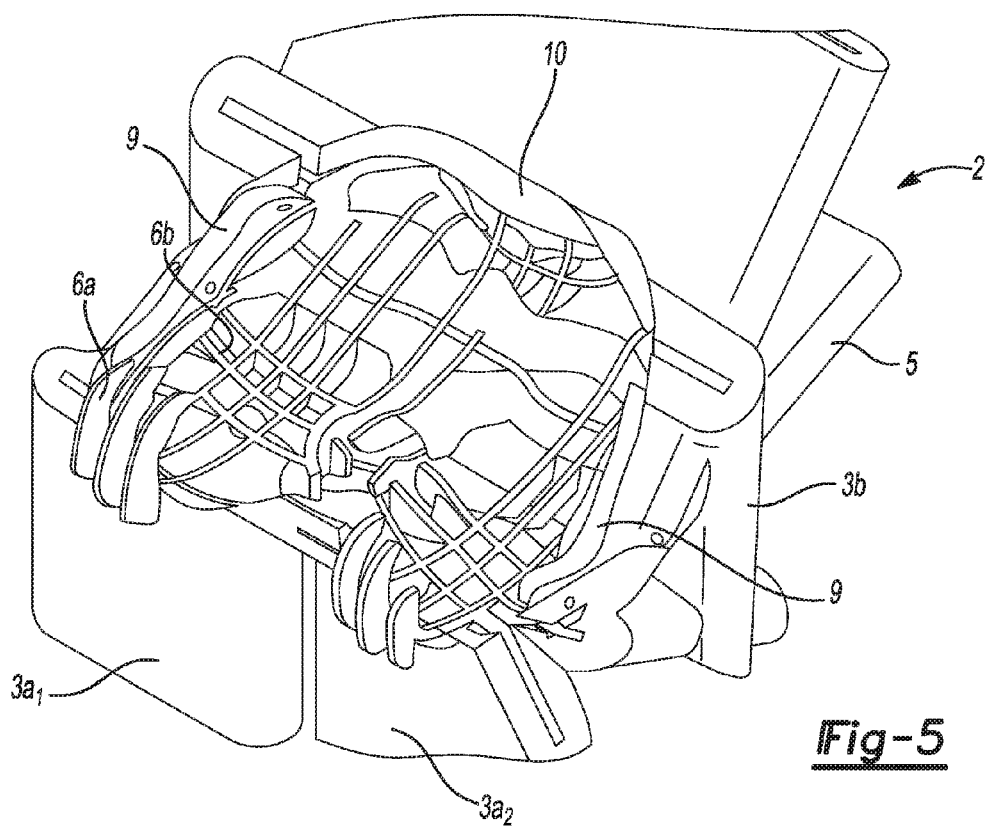
Figure 6:
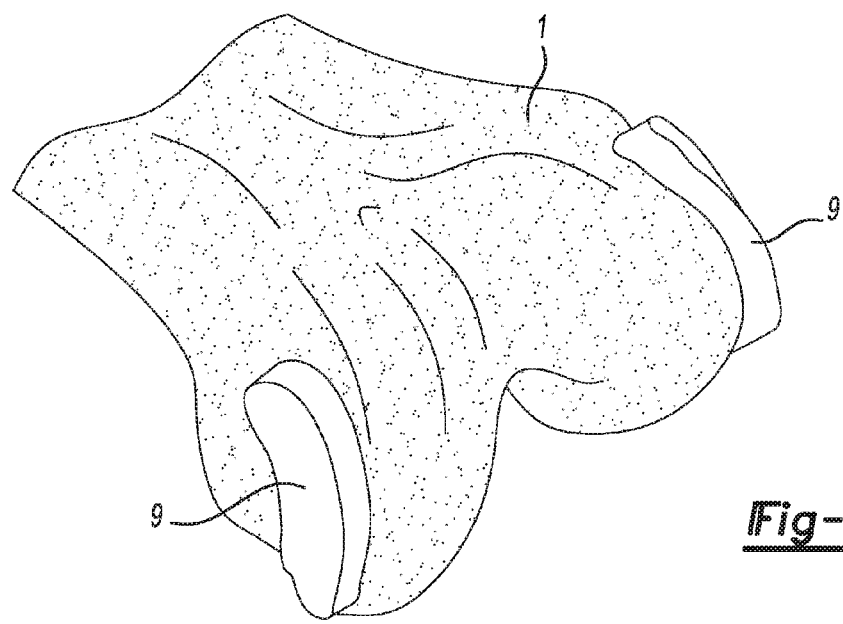
Figure 7:
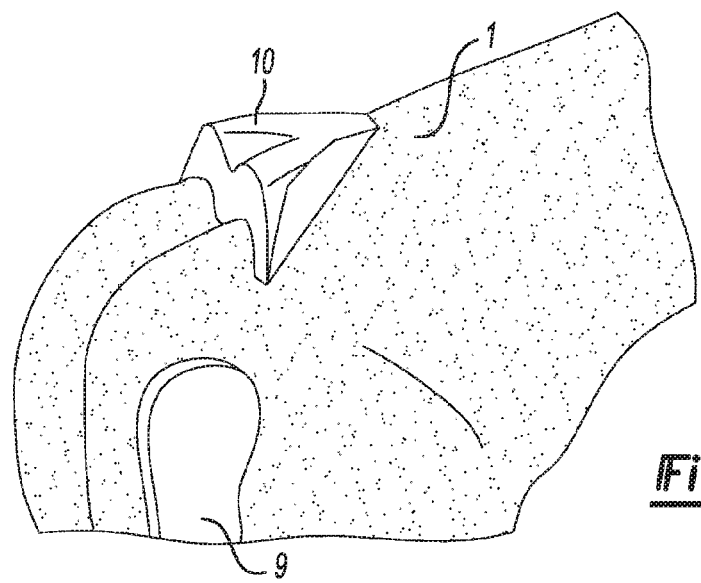
Figure 8:
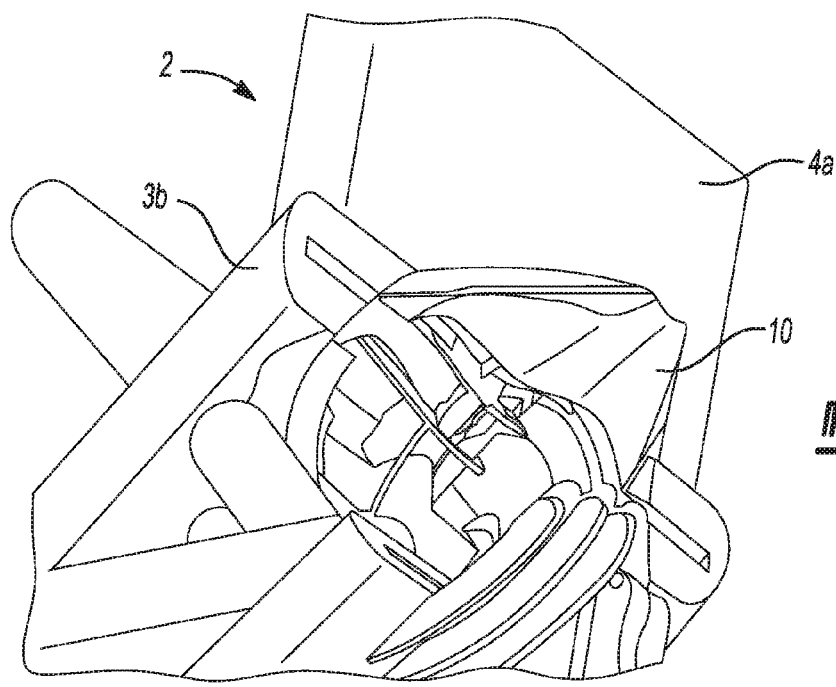
Figure 9:
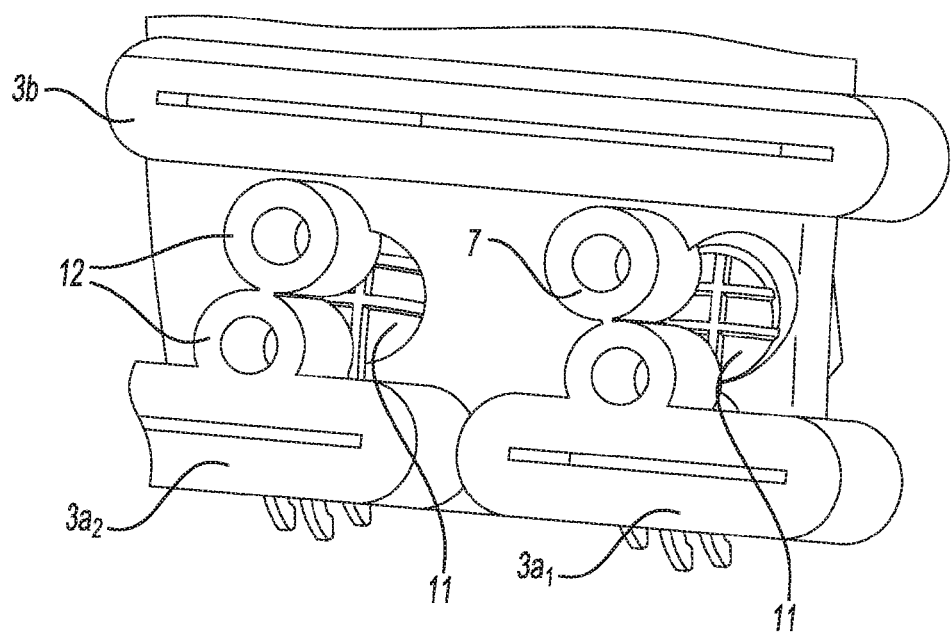
Figure 10:
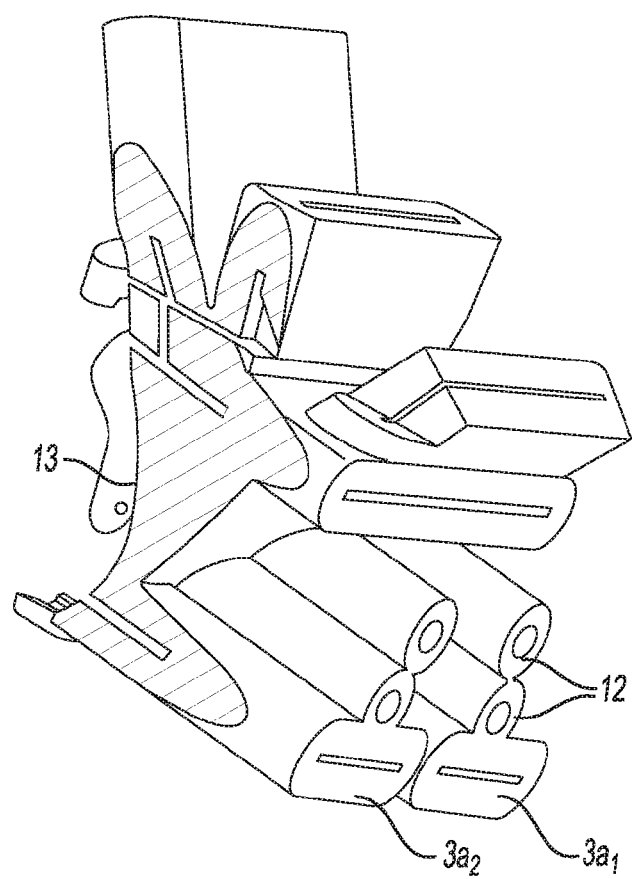
Figure 12:
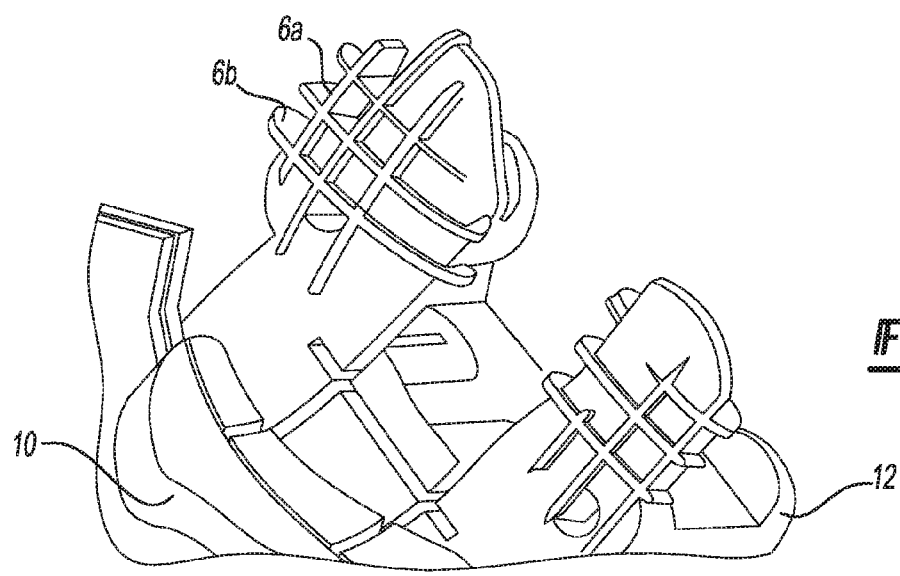
Figure 13:
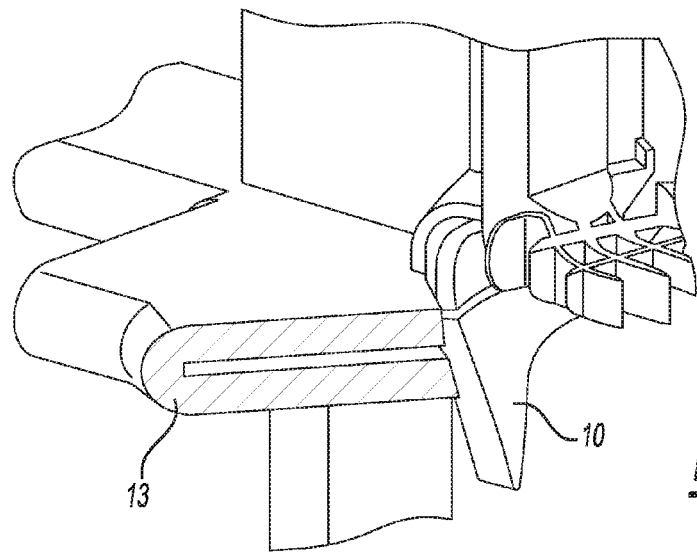
Figure 14:
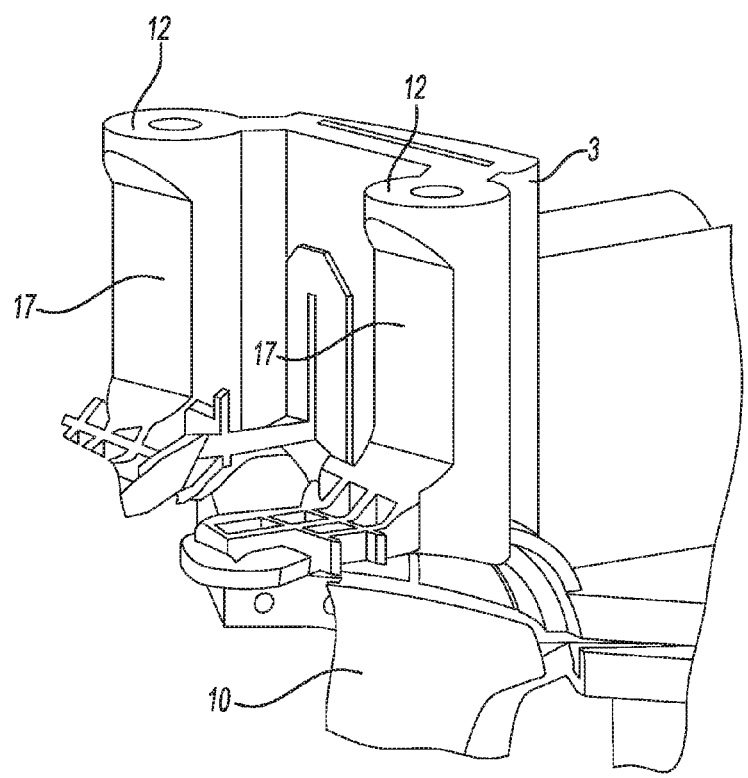
Figure 15:
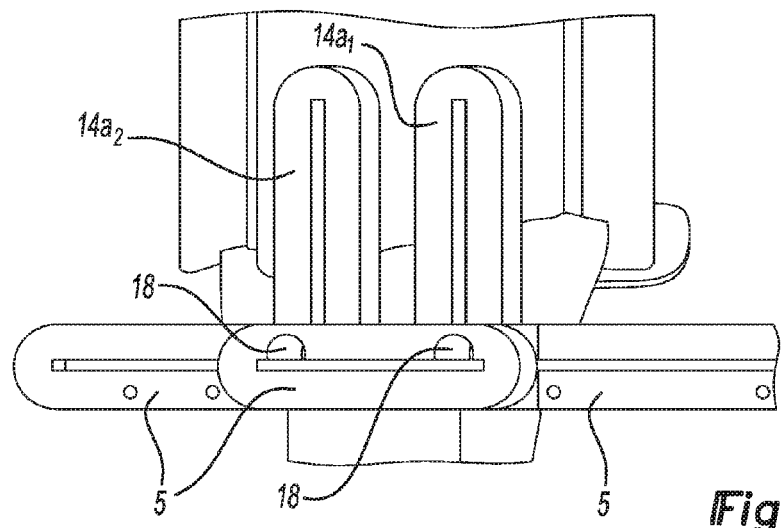
Figure 16:
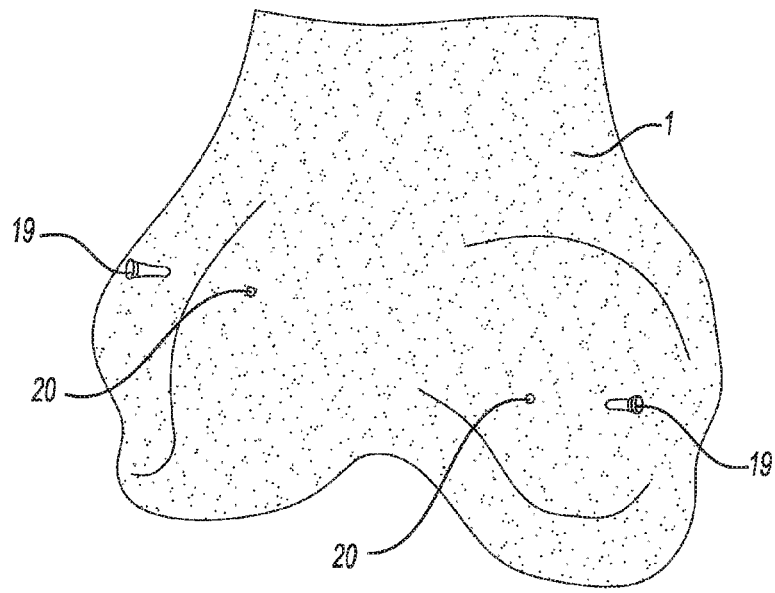
Figure 17:
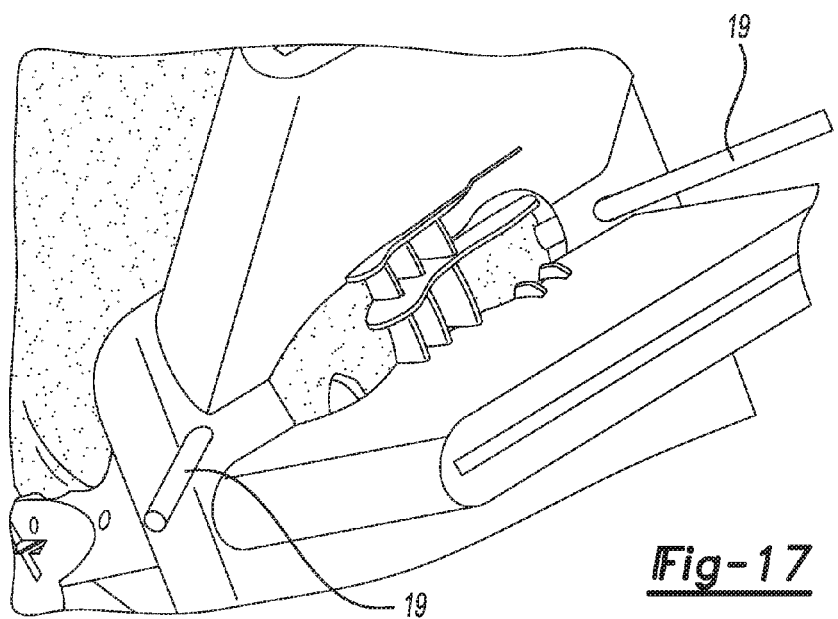
Figure 18:
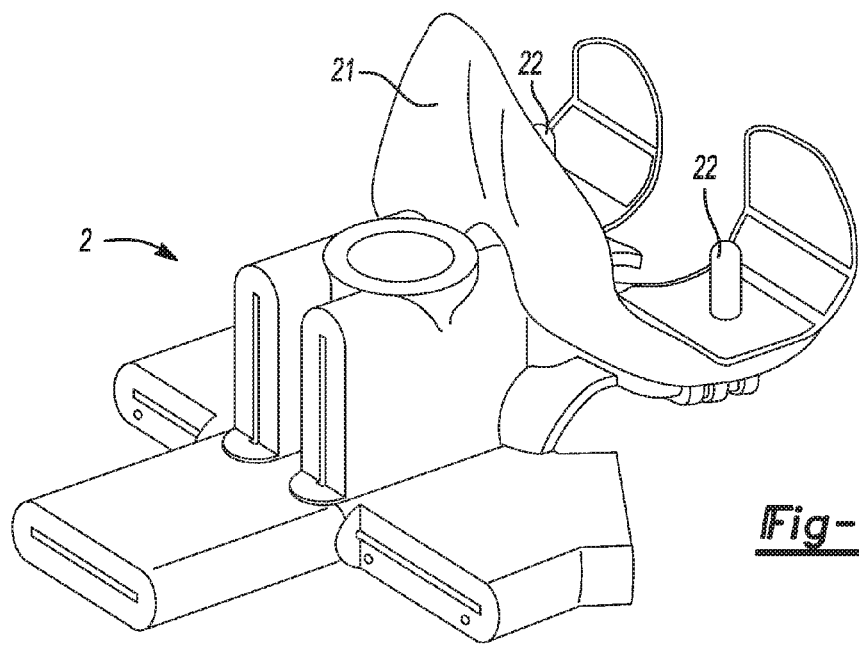
Figure 23:
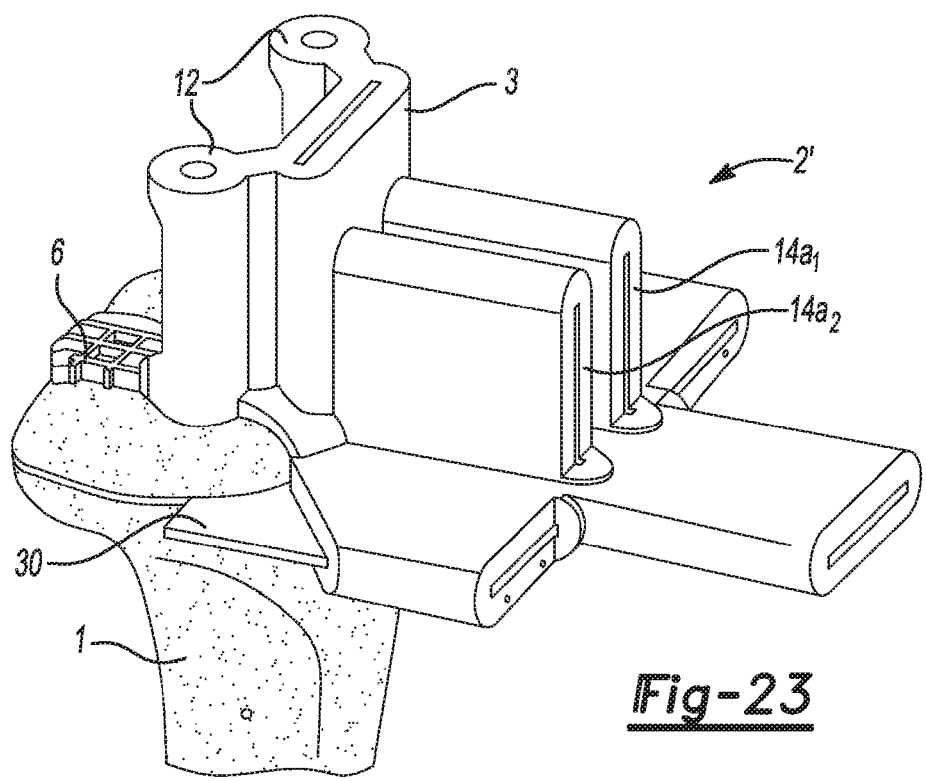
Figure 24:
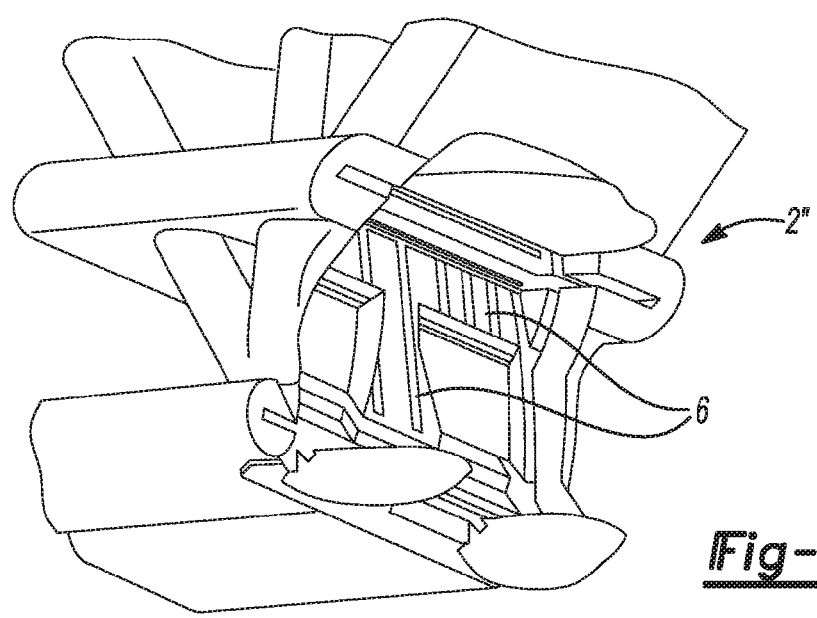

Some preferred embodiments of the present invention are further explained in the enclosed figures. Showing:

FIG. 1 The three-dimensional view of an inventive device with bone,

FIG. 2 a schematic cross section of the inventive device with bone,

FIG. 3 a cross section of the inventive device with bone,

FIG. 4 a three-dimensional top view of the bone with inventive grid-shaped supports, FIG. 5 a schematic top view of an inventive device with inventive grid-shaped supports, FIG. 6 a femur bone with lateral template brackets, FIG. 7 a femur bone with template muzzle, FIG. 8 a three-dimensional sectional view of the inventive device with template muzzle, FIG. 9 the top view of an inventive template, FIG. 10 the three-dimensional cross section of an inventive template with tailored tool guides, FIG. 11 the three-dimensional view of a tibia template, FIG. 12 the three-dimensional partial view of the tibia template of FIG. 11, FIG. 13 the three-dimensional schematic cross section of a tool guide of the tibia template of FIG. 11, FIG. 14 the three-dimensional schematic cross section on special supporting surface areas of the tibia template, FIG. 15 the three-dimensional back view of a tibia template, FIG. 16 a femur bone with marker pins, FIG. 17 a three-dimensional top view on a template with fixing pins and bones, FIG. 18 the three-dimensional view of a tibia template with adjusted femur endoprosthesis, FIG. 19 schematic bottom view of a tibia template, FIG. 20 the view of a drilling template for tibia pins, FIG. 21 the view of a two-dimensional tibia socket, FIG. 22 the view of a two-dimensional tibia template, FIG. 23 the three-dimensional view of a modified tibia template, and FIG. 24 the three-dimensional view of a modified inventive device without bones.

FIG. 1 shows the three-dimensional cross section of an inventive device for the resection of a femur bone 1 with several tool guides 3, 4, 5 and inventive supports 6. For the treatment of a knee joint damage, the femur bone is generally resected in different areas. For this, the femur bone is cut off at various levels in order to cut off the abnormal cartilage or bone surface. According to an initial tool guide 3a, 3b, the cut surfaces are located in the coronary area and resect the thigh bone 1 on the site turned towards the knee joint as well as on the opposite side. Furthermore, the inventive device shows a third tool guide 5 which is basically perpendicular to the first tool guide 3a, 3b which is transversal to the femur bone. This tool guide serves for the insertion of a saw for the cutting off the distal ends of the femur bone 1. The second tool guides 4a, 4b are arranged angularly to the initial tool guide 3a, 3b and to the third tool guide 5 which are canthomeatal (acute-angled to the transverse plane) of the femur bone 1, preferably with an inclination of about 45° to the third tool guide 5 which is arranged transversely.

All tool guides 3a, 3b, 4a, 4b, 5 build an immovable tool guide template aligned to each other in a fixed angle which also feature supports 6 which are shaped relatively to the tool guides for the exact attachment to the bone 1.

FIG. 2 displays a three-dimensional, schematic cross section of an inventive device, in particular a resection template 2 with coronary tool guides 3a, 3b and a canthomeatal tool guide 4b, which are acute-angled to leach other and enable the preparation of certain bone surfaces of the femur bone. Every tool guide preferably features a guide stop 27 which defines the exact immersion depth of the tool. The tool, for example a saw, is inserted into the tool guides, for example, a saw core, which possess guidance depth D. Once the tool has overcome the guidance depth D, the cutting into the bone until resection depth d takes place. Guidance depth D and resection depth d result in immersion depth t of the tool. The exact adjustment of the guidance depth D to the tool guarantees that not too little and not too much bone is cut off and accordingly the soft tissue behind the bone, such as tendons, ligaments or blood vessels, is not damaged. The lateral core limitation of the tool additionally guarantees the very important protection of the sidebands of the knee joint during bone resection.

The manufacturing technique of the inventive resection template 2 makes it possible to manufacture the tool guides, such as the resection cores or drill holes, in exactly the lengths in which a precise immersion depth t of the tool can be determined.

FIG. 3 displays a cross section of the inventive resection template 2 with coronary tool guides 3a and 3b as well as canthomeatal tool guide 4b whereas whereas the cores 8 which are suitable for a saw can be recognized. Furthermore, FIG. 3 displays a fourth tool guide 7 which is, for example, appropriate for a drill which is used for undertaking an appropriate drill in the bone in order to take in support pins of the endoprosthesis. Through the hole, a recess 23 can be made in the bone which serves for attaching the endoprosthesis. At the same time, FIG. 3 displays vertically (marked three-dimensionally on it) linear supports 6 which are described in more detail below:

FIG. 4 shows the three-dimensional view onto the distal end of the femur bone 1, where the linear supports 6 can be seen. For a better representation, the other parts of the resection template 2 are not illustrated. The grid-shaped, linear supports 6 are basically rectangular whereas sagittal ribs 6a and coronary ribs 6b are basically perpendicular to each other and display the basic structures of the bone.

The exact positioning of the resection template 2 takes place with the help of a grid-shaped structure of linear supports 6. In order to achieve an optimal reproduction of the surface structure of bone 1 and in order to position the later template 2 precisely to the bone 1, for example, a computer-tomographic image is taken which displays the different layers of the bone. By means of this computer-tomographic image, two-dimensional, linear differences in gray value can be detected which mark the crossing between bones and soft tissue. Along the layered images, the linear supports 6 can be reconstructed by scanning and molding the bone surface along the two-dimensional tomographic layered images. This rib construction has the advantage that only precise landmarks of the bones can be depicted whereas the effort for the reconstruction of the joint surface negative is reduced significantly. Furthermore, an exact support of the resection template 2 on bone 1 can be guaranteed because soft tissue or synovial fluid not sufficiently captured by computer-tomographic images can be eluded between the ribs or the ribs can be pushed easier into elevated surface areas until they encounter the bone surface or the ribs can be pushed away from the elevated surface areas.

The rib structure schematically displayed in FIG. 4 shows FIG. 5 embedded in resection template 2. Between the initial tool guides 3a and 3b, placed parallel to each other, the second tool guides 4a and 4b and the third tool guides 5, the grid-shaped supporting structure 6 of the sagittal ribs 6a and the diagonally-shaped coronary ribs 6b is visible. Two coronary tool guides 3a 1 and 3a 2, which are divided from each other, are used for the resection of two bone humps on the distal end of the femur bone 1.

In a computer-tomographic image of the femur, the cartilage covering between both femoral condyles up to the beginning of the knee joint slide bearings is generally conserved, thus enabling arch-shaped structures to be reconstructed by tracing of the surface in sagittal direction, for example, in three ways, which have, for example, a width of three layers which cause a hooking of the resection template to the bone surface. As a result, an upward sliding and a sideway sliding is prevented, this makes it possible to position template 2 precisely.

FIG. 6 shows second supports 9, for example, coronary brackets, which can be implemented as lateral template brackets. This serves the purpose of a defined attachment of the resection template 2 in lateral direction on the distal end of the femur bone. This provides support for the coronary ribs 6b which are arranged on coronary level or by the second supports which are displayed in FIG. 6 and built as coronary brackets and which are constructed on the left and right side of the outer side of the femur.

While reconstruction the second support, care has to be taken that the coronary brackets do not come into contact with the external or internal sideband with an approximate 110° flexion of the knee joint after opening the knee joint and everting the knee cap but to circle the epicondyl humps above and ventrally and to not reach to close to the joint margins in order not to conflict with possible osteopyths present. In order to take the skin of the bone and the remaining mucosa into consideration, for example, 0.2 mm needs to be deducted from the bone side of this construction.

FIGS. 7 and 8 show a third support 10, which is shaped as a sagittal muzzle, in order to secure the resection template 2 in sagittal direction. Thereby, a third support, especially above the kneecap slide bearings, is manufactured, which narrows towards the top, that is, proximal. This template beak must not be too long in order not to damage the upper recessus or musculus articularis not too much. The anchorage of the third support 10 to the resection template 2 has to be made in such a way that the anchorage does not close up the initial coronary tool guide 3b. The template muzzle can be constructed from an extension of tool guide 3b.

FIG. 9 shows the top view of the inventive device with two-part coronary tool guides 3a 1 and 3a 2 as well as initial coronary tool guides 3b, arranged parallel to it but at the same time at a distance to each other, and which are appropriate for a saw as well as two viewing openings 11 which allow the view of the grid structure of the linear support 6 and the surgical area. Additionally, FIG. 9 shows fixation openings 12 which are distally located on the template in order to introduce fixatives.

In the special example of embodiment according to FIG. 9, on the distal area of the resection template 2, for example, two cylindric cores, 3 to 4 cm in diameter, are arranged which enable the view of the underlying joint area and allow to control if the templates are level with the surface, thus, if the linear supports 6 are level with the bone surface.

A considerable complication of knee surgery is the accidental resection of the anterior cruciate ligament. Whereas with conventional bicondular knee joint endoprosthesis, the anterior cruciate ligament is generally resected, the anterior cruciate ligament can be preserved with individually manufactured knee joint endoprostheses, according to the present invention. In order to avoid an accidental damage of the cruciate ligaments, an opening is adjusted on the femur template which, for example, has a diameter of 3 to 4 cm, is round and is in line with the projection on the intercondylar notch. The opening gives a view of the anterior cruciate ligament and also gives the possibility of protecting the anterior cruciate ligament by using chirurgical instruments at each resection. Additionally, this opening gives a view of the positioning of the ribs, of the so-called notch hook and also partly on the supports 6 of the margin of the under femoral condyle.

According to FIG. 10, the tool guides 3, 4, 5, 7, 14 can be also tailored in order to avoid a displacing of the template on the open situs by lateral everted soft tissue. The tailoring should be made on the side of the knee joints and the soft tissue in order to avoid a displacing of the template.

Furthermore, the invention also applies to a tibia template, schematically displayed in FIG. 11, with fifth tool guides 14 a1 and 14 a2 which are separated from each other as well as a coronary tool guide 3 and a transversal tool guide 5. Also, the linear supports 6 as well as the fixation guides 12 for the fixing of the template to the bone are indicated. By the use of these fixation guides 12, for example, nails or screws can be guided in order to guarantee the support of the template. The precise positioning and adjustment of the template takes place by means of the linear supports 6, though.

The supports 6 can also be featured as grid structure, as displayed in FIG. 12, whereas the sagittal ribs 6a and the coronary ribs 6b build the grid structure which are arranged preferably rectangular to each other. In this regard, it is important to approximate the supports 6 as close as possible to the intercondylar humps in order to achieve a certain lateral stabilization.

Equally, in FIG. 11 a bridge 15 is displayed which leads to a supporting surface area 16 which can be arranged punctually, if necessary, or—as displayed in FIG. 11—flat, whereas it is not a template bracket with a so-called tibia bow which is situated from the surgical situs towards the outside and presses the supporting area on the intact, skin-covered surface of the tibia. Therefore, a rotation of the tibia template 2 along the lateral axis and the vertical axis in an anteroposterior direction as well is prevented.

In this version of the invention, a resection of the tibia takes place with the help of a template according to FIG. 11, whereas the opening for the femoral condyle needs to be proceeded further. In the second step, a template, which is a combination of FIG. 1 and FIG. 2, is manufactured, and presents a polyamide model of the tibia component of the endoprosthesis and is linked inseparably to a saw guide for the resection on the thigh bone, whereas with one of the initial templates, only the cut on the thigh bone in extension position and at a distance from the body (distal) is permitted, and with a second template, only the rearward (dorsal) cut on the femoral condyle in flexion position is permitted.

According to the above mentioned method (femur first), the axis (in extension position) is adjusted initially and subsequently, the ligamentous tension (in extension and flexion position) is balanced. Subsequently, with an appropriate third template, the so-called folding cuts are performed and thus, the resection of the thigh bone is completed.

This method (tibia first) is also appropriate for the implantation of standardized endoprostheses because a lower leg component (a tibia plateau) can be inserted without the need of adjusting it completely to the surface contour of the original tibia plateau.

With the "femur first" method, a similar device for the tibia—used as "tibia stopper" (but as a straight, horizontal limitation passing before the tibia bone, for example, in the shape of a cylindric rod)—can display the precise extension position of the knee joint which has been fixed pre-operatively on the image data instead of the sleeve-like support adapted to the shinbone which is inseparably attached to the thigh template.

This is helpful in cases where a more or less large degree of extension deficits of the knee joint due to ligament shortening is present. These extension deficits are solved with the compensation of the ligamentous tension, in full or in part, and thus, a changed position of the extension position compared to the position at the time of imaging is the result. The straight shape of this tibia support permits a swinging of the lower leg at the adjustment of the leg axis and at the correction of the ligamentous tension in contradiction to the sleeve-shaped support.

Additionally, a third support 10 can be intended as a so-called tibia plate which is constructed as a bracket-like support on the front edge of the tibia in order to guarantee a precise locating and positioning of the resection template 2 in anteroposterior direction. The third support 10 should be molded medially next to the tibia hump, as far as possible, in order to avoid a lateral rotation in lateral position of the template 2 around the vertical axis and to guarantee a positioning around the vertical axis as precisely as possible. In order to examine the leveled position of the third support 10 conducted as tibia plate, an opening medial to the tuberositas tibia can be attached.

FIG. 13 displays the lateral tailoring 13 of a tool guide of the tibia template in order to avoid a movement of the template caused by laterally everted soft tissue. Furthermore, according to FIG. 14, it is possible to mold the rearward side of the tibia template by a support 17 in such a way that it corresponds exactly to the resected surface of the distal end of the femur 1 which is located in a 110° flexion position close to the tibia bone. This supports an exact positioning of the resection template 2 on the tibia bone. It is possible because the joint space is very narrow by preservation of the anterior cruciate ligament and the tibia template could otherwise be moved by the femur ventral.

FIG. 15 shows the schematic top view of the tibia template with 15 sagittally adjusted tool guides 14 a1 and 14 a2 as well as a transversal tool guide 5, whereas sagittal canals 18 are provided which enable the use of appropriate Kirschner's wires or Steinmann's nails to an interface between the vertical resection level at the intercondylar humps and the horizontal resection area on the tibia plateau. This not only enables an additional fixation of template 2 on bone 1 but also prevents an accidental sawing too deep inside the so-called intercondylar humps during the horizontal resection or a very deep sawing inside the tibia head during the vertical resection. It would cause a significant complication because generally, a fracture of the intercondylar hump or a fracture of the inner or outer kneecap bracket would be the result. In order to guarantee an exact positioning of the resection template 2, additional fastening means 19 or fastening areas 20 can be attached to the bone 1, according to FIG. 16, such as markers, like screws, Kirschner's wire or pins, which can be inserted into the appropriate template mounting when adjusted to the bone.

FIG. 17 shows the implementation of appropriate fastening means 19 by appropriate openings of the resection template 2.

FIG. 18 displays the three-dimensional top view of an inventive resection template 2, a tibia template in particular, which is molded to an endoprosthesis 21. The embodiment of the present invention is used for the exact positioning of the tibia template towards the prospective implanted femur prosthesis 21. One end of template 2 represents a reproduction of the femur prosthesis 21 which features pins 22 for the insertion in, for example, recesses 23 as displayed in FIG. 3. After the resection of the femur, the tibia template which is molded as endoprosthesis 21 is adapted to the femur similar to femur prosthesis and, after full extension and exact positioning of the tibia according to the Mikulic'z-line and after fixation of bone 1, is attached to the template 2 with the help of Kirschner's wires. This enables a precise resection of the tibia even without fastening means 19, such as marker screws.

FIG. 19 displays the three-dimensional view of a resection template 2 which features a guiding aid 24 besides the third support 10 which, for example, is a guiding aid for a measuring stick for the precise determination of the Mikulic'z-line whereas this guiding aid runs through the proximal part of the tibia template, in particular. The guiding aid 24 in shape of a hourglass drill runs in vertical direction and its narrowest position stands exactly in front of the knee joint focus, so that after inserting a long measuring stick or measuring tape, a straight line between the focus of the femur head, the knee joint focus and the focus of the ankle joint can be identified.

FIG. 20 shows a drill guide 26 which is featured in a tibia template 25 which, for example, is for the attachment to the resected bone. For example, after removal of the femoral tibia template 2, the anterior part of the intercondylar hump needs to be resected with the oscillating saw and the edges need to be smoothed with a round file, so that the front bracket between both plateaus of the tibia frame can be moved forward to the tibia plateau that a precise adjustment of the tibia frame on the resected tibia bone is guaranteed. On this occasion, corrections of the fit of the tibia frame can be made, for example, smaller corrections with the use of a straight file on the front or lateral edges of the intercondylar hump. With the help of the drill holes of the template, the anchoring canals for the pins of the tibia plate can be drilled, eventually.

FIG. 21 displays an alternative, which is, a two-part tibia frame with pins 22 which can be implanted, so that a resection of the central part of the intercondylar hump is unnecessary. However, the tibia template 25 needs to consist of two parts as well according to the tibia frame 28 which are connected with a brace 29, running in front of the intercondylar humps. FIG. 22 displays the embodiment of drill guides 26.

At implantations with the preservation of the anterior cruciate ligament, i.e. implantations of individual endoprosthesis, there is generally not enough space for implementing the vertical stops at the tibia without damaging the femur or cutting too deep into the tibia. The preservation of the anterior cruciate ligament always means confined space in the joint lines during surgery because the anterior cruciate ligament prevents a sliding of the tibia towards the femur. Furthermore, with the use of the resection template 2, the knee joint is kept in extension position which means an additional narrowing of space.

For this purpose, the resection template 2, as shown in FIG. 11, is modified by excluding the bridge 15 and all tool guides as far as the transversal, third tool guides 5. Subsequently, the horizontal steps can be taken. Afterwards, the tool guides 3, 14a1, 14a2 for the vertical cuts on the tibia, are attached with the help of a further modified resection template 2', as shown in FIG. 23. The transversal, third tool guides 5, which are also shown, can also be excluded from the modified resection template 2' (not shown in FIG. 23). Because of the possible flexion of the knee joint and the non-support of the prosthesis imitation in the resection areas of the femur, as displayed in FIG. 18, the joint has more flexibility and sufficient space in order to guarantee the vertical cuts without additional damage of the bone structure.

The attachment of the modified resection template 2' on the tibia, according to FIG. 23, can additionally be made with two insertion-style plates 30, which are inserted into the horizontal resection gaps which are already prepared. This enables an even more precise positioning.

FIG. 24 displays the three-dimensional view of a modified inventive device without bone for the revision surgery. Generally, after 10 to 12 years, a loosening of the prosthesis takes place. In these cases, the old prosthesis needs to be removed, a new implant socket needs to be created and a bigger, new prosthesis, as appropriate, needs to be implanted. Despite the loosening of the old prosthesis, after removal of the old prosthesis the implant socket basically remains the same as before the initial implantation, so, according to FIG. 24, another modified template 2" can be leveled to the old implant socket. In accordance with the invention, appropriate supports 6 are provided but because of the smooth surface of the implant socket not absolutely essential. The modified template 2" shows only tool guides for saw blades which enable an appendectomy of, for example, 2 mm on each level of the implant socket. Thus, a new implant socket for conventional or even individually manufactured alteration prosthesis can be prepared precisely and in a time and/or bone saving way.

The invention claimed is:

1. A device for preparing a bone for an implant comprising:
    a support portion comprising a plurality of elongate elements shaped as a reproduction according to corresponding elongate surface structures of the bone from a three-dimensional image of the bone, the plurality of elongate elements arranged to form cavities that can engage anatomy of the bone; and
    a tool guide portion attached to the support portion, the tool guide portion including a first tool guide oriented and positioned by the support portion to prepare an area of the bone for receiving an implant.

2. The device of claim 1, wherein the plurality of elongate elements includes a first plurality of spaced-apart sagittal elements and a second plurality of spaced-apart coronary elements forming a grid.

3. The device of claim 2, wherein the first tool guide includes a planar surface configured to guiding a resection of the bone along a plane for receiving an implant.

4. The device of claim 2, wherein the tool guide portion includes a plurality of tool guides.

5. The device of claim 2, wherein the tool guide portion includes a second tool guide configured for guiding fixation elements.

6. The device of claim 2, wherein the device is a tibial template and further comprising a support surface for a tibial bone, the support surface spaced apart from the support portion and attached to the support portion with an elongated bridge element.

7. The device of claim 2, wherein the device is a femoral template and includes a pair of lateral brackets supporting the coronary elements.

8. The device of claim 2, wherein the device is a tibial template and the support portion is shaped as a reproduction of a femoral knee implant.

9. The device of claim 2, wherein the sagittal elements are substantially parallel.

10. The device of claim 2, wherein the coronary elements are substantially parallel.

11. The device of claim 2, wherein the sagittal elements are substantially parallel and perpendicular to the coronary elements.

12. A device for preparing a bone for an implant, comprising:
    a support portion including a plurality of elongate elements shaped as a reproduction according to corresponding elongate surface structures of the bone from a three-dimensional image of the bone;
    a first tool guide portion including a first sagittal tool guide and a second sagittal tool guide, the first and second sagittal tool guides parallel to each other and configured to cut a sagittal area of the bone;
    a second tool guide portion including a coronary tool guide, the coronary tool guide being substantially perpendicular to the first and second sagittal tool guides; and
    a third tool guide portion including a transverse tool guide, the traverse tool guide being substantially perpendicular to the first tool guide portion and the second tool guide portion.

13. The device of claim 12, wherein the plurality of elongate elements are arranged to form at least one viewing opening through the device between adjacent elongate elements.

14. The device of claim 12, further comprising a bridge extending from one of the first, second or third tool guide portions.

15. The device of claim 14, wherein the bridge extends from the transverse tool guide away from the first and second sagittal tool guides substantially parallel to the coronary tool guide.

16. The device of claim 15, wherein the bridge includes a supporting surface area for engaging a portion of a lower leg.

17. The device of claim 12, further comprising a tibia plate extending from the support portion and comprising a support configured to engage a front edge of a tibia.

18. The device of claim 12, further comprising lateral tailoring of one of the first, second or third tool guide portions configured to retract the one of the first, second or third tool guide portions from bone to avoid soft tissue engagement of the device.

19. The device of claim 12, further comprising:
- a fixation guide extending along the coronary tool guide; and
- a plurality of support surfaces disposed along the fixation guide and shaped to engage corresponding surfaces of a resected femur.

20. The device of claim 12, further comprising a pair of sagittal canals extending along the transverse cutting guide.

21. The device of claim 12, further comprising an endoprosthesis connected to the support portion.

22. The device of claim 21, wherein the endoprosthesis comprises a reproduction of a femur prosthesis.

23. The device of claim 12, further comprising a pair of insertion-style plates extending from the transverse tool guide and configured to be inserted into horizontal tibia resection gaps.

24. The device of claim 12, wherein the plurality of elongate elements are arranged to form cavities that can engage anatomy of the bone.

25. The device of claim 12, wherein each of the plurality of elongate elements is elastic.

* * * * *

UNITED STATES PATENT AND TRADEMARK OFFICE
CERTIFICATE OF CORRECTION

| | | |
|---|---|---|
| PATENT NO. | : 9,839,433 B2 | Page 1 of 1 |
| APPLICATION NO. | : 15/183349 | |
| DATED | : December 12, 2017 | |
| INVENTOR(S) | : Luis Schuster | |

It is certified that error appears in the above-identified patent and that said Letters Patent is hereby corrected as shown below:

On the Title Page

Item (30), in "Foreign Application Priority Data", in Column 1, Line 1, delete "10 2009 028 503" and insert --10 2009 028503.2-- therefor Signed and Sealed this
Fourth Day of June, 2019

Andrei Iancu
*Director of the United States Patent and Trademark Office*